(12) United States Patent
Li et al.

(10) Patent No.: US 11,724,016 B2
(45) Date of Patent: Aug. 15, 2023

(54) VENOUS AIR CAPTURE CHAMBER

(71) Applicant: Medtronic, Inc., Minneapolis, MN (US)

(72) Inventors: Zhigang Li, Shanghai (CN); Mark Daniels, Lino Lakes, MN (US); Thomas E. Meyer, Stillwater, MN (US); Huande Liu, Hangzhou (CN)

(73) Assignee: Mozarc Medical US LLC, Minneapolis, MN (US)

( * ) Notice: Subject to any disclaimer, the term of this patent is extended or adjusted under 35 U.S.C. 154(b) by 1197 days.

(21) Appl. No.: 16/308,640

(22) PCT Filed: Jun. 23, 2016

(86) PCT No.: PCT/CN2016/086844
§ 371 (c)(1),
(2) Date: Dec. 10, 2018

(87) PCT Pub. No.: WO2017/219311
PCT Pub. Date: Dec. 28, 2017

(65) Prior Publication Data
US 2019/0175815 A1    Jun. 13, 2019

(51) Int. Cl.
*A61M 1/36* (2006.01)

(52) U.S. Cl.
CPC ............ *A61M 1/3627* (2013.01); *A61M 1/36* (2013.01); *A61M 1/3644* (2014.02); *A61M 2206/10* (2013.01)

(58) Field of Classification Search
CPC .... A61M 1/36; A61M 1/3621; A61M 1/3627; A61M 1/3644; A61M 1/3667; A61M 2206/10
See application file for complete search history.

(56) References Cited

U.S. PATENT DOCUMENTS 4,102,655 A    7/1978   Jeffery et al.
4,368,118 A *  1/1983   Siposs ................. A61M 1/3627
                                                  96/208
(Continued)

FOREIGN PATENT DOCUMENTS

CN    1116956 A     2/1996
CN    202154892 U   3/2012
(Continued)

OTHER PUBLICATIONS

Japanese Office Action for App. No. 2018-566313, dated Apr. 22, 2020.
(Continued)

*Primary Examiner* — Philip R Wiest
(74) *Attorney, Agent, or Firm* — Hahn & Associates

(57) ABSTRACT

A venous air capture chamber for use in dialysis, includes an upwardly extending fluid inlet terminating in first and second fluid inlet ports (102). The first and second fluid inlet ports (102) are opposedly positioned on the fluid inlet at an angle of about 180°. The venous air capture chamber also includes a fluid outlet (104) at the bottom of the chamber body. The venous air capture chamber provides improved fluid dynamics, reducing both stagnant flow and turbulence. The venous air capture chamber also provides for bidirectional flow of fluid through the chamber.

20 Claims, 39 Drawing Sheets

(56) References Cited

U.S. PATENT DOCUMENTS

| | | | | |
|---|---|---|---|---|
| 4,493,705 | A | * | 1/1985 | Gordon ............... A61J 1/10 |
| | | | | 604/122 |
| 4,622,032 | A | * | 11/1986 | Katsura ............ A61M 1/3627 |
| | | | | 604/122 |
| 4,643,713 | A | * | 2/1987 | Viitala ............. A61M 1/3627 |
| | | | | 96/155 |
| 4,681,606 | A | | 7/1987 | Swan, Jr. et al. |
| 4,734,269 | A | * | 3/1988 | Clarke .............. A61M 1/3627 |
| | | | | 96/219 |
| 5,328,461 | A | * | 7/1994 | Utterberg ........... A61M 1/3627 |
| | | | | 95/260 |
| 5,573,526 | A | * | 11/1996 | Hess ................. A61M 1/3624 |
| | | | | 604/122 |
| 5,707,431 | A | | 1/1998 | Verkarrt et al. |
| 5,849,065 | A | * | 12/1998 | Wojke .............. A61M 1/3627 |
| | | | | 96/219 |
| 6,051,134 | A | | 4/2000 | Schnell |
| 6,053,967 | A | * | 4/2000 | Heilmann .......... A61M 1/3627 |
| | | | | 96/216 |
| 6,117,342 | A | * | 9/2000 | Schnell ............. A61M 1/3627 |
| | | | | 210/801 |
| 6,337,049 | B1 | * | 1/2002 | Tamari ............. A61M 1/3667 |
| | | | | 604/4.01 |
| 6,478,962 | B1 | | 11/2002 | Brockhoff |
| 6,562,107 | B2 | * | 5/2003 | Purdom ........... B01D 19/0047 |
| | | | | 96/219 |
| 7,559,911 | B2 | * | 7/2009 | Giannella ......... A61M 1/3627 |
| | | | | 604/408 |
| 10,709,637 | B2 | * | 7/2020 | Spro ................. A61J 1/1481 |
| 2014/0217027 | A1 | | 8/2014 | Meyer | |

FOREIGN PATENT DOCUMENTS

| | | |
|---|---|---|
| CN | 203342108 U | 12/2013 |
| CN | 10376419 | 4/2014 |
| EP | 2540328 A1 | 1/2013 |
| GB | 1544810 | 4/1979 |
| JP | 07204408 | 8/1995 |
| JP | 2002-512553 | 4/2002 |
| JP | 2008-246081 | 10/2008 |
| JP | 2011092498 | 5/2011 |
| WO | WO 2005/044339 | 5/2005 |
| WO | WO 2008-053261 | 5/2008 |

OTHER PUBLICATIONS

Search Report for Brazilian App. No. BR112018076977-0, dated Mar. 18, 2020.
Office Action for Japanese Application No. 2018-566313, dated Nov. 27, 2020.
International Search Report for PCT/CN2016/086844 date of completion is Feb. 24, 2017 (3 pages).
European Search Report for App. No. 16905852.6, dated Jan. 20, 2020.
International Search Report for PCT/CN2016/086843 (dated Feb. 25, 2017).
OA 201680087009.8.
European Search Report for App. No. 16905852.6, dated May 12, 2020.
Japanese Office Action for App. No. 2018-566314, dated May 8, 2020.
Brazilian Office Action for App. No. BR112018076718-2, dated Jun. 10, 2020.

* cited by examiner

VENOUS AIR CAPTURE CHAMBER

FIELD OF THE INVENTION

The invention relates to a venous air capture chamber for use in dialysis. The venous air capture chamber reduces both stagnant flow and turbulence, and provides improved capture of air bubbles from liquid flowing through the chamber. The venous air capture chamber further provides for bidirectional flow to automate aspects of system priming.

BACKGROUND

Venous air capture chambers are used in hemodialysis to separate entrained air bubbles from the blood before the blood is returned from the dialyzer to the patient. Conventional venous air capture chambers suffer from both areas of stagnant flow within the chamber and from areas of mixing between blood and air resulting in an increased tendency to coagulation in the extracorporeal circuit. Often, a turbulent blood surface is in contact with air in a manner such that air is further entrained into the blood which promotes mixing of air into the blood resulting in thrombosis activation, clogging of the dialyzer, and microbubbles that can be passed to the patient receiving a hemodialysis treatment. Moreover, red blood cells can be damaged due to the high shear stresses. Shear stress is aggravated when blood flows at an increased rate into the venous air capture chamber. As such, conventional chambers fail to inhibit blood coagulation and/or undesirably activate blood thrombosis.

Conventional priming of a dialysis system is a complex process which requires training and monitoring. Automated priming is not used in conventional venous air capture chambers because fluid can only flow in one direction. Dialyzer priming removes air from the dialyzer prior to use. In general, the dialyzer must be inverted or "flipped" during priming to facilitate air removal from the dialyzer compartment. Then, with the dialyzer inverted, a physiologically compatible saline solution is introduced from the bottom of the dialyzer to drive air out the top of the vertically positioned dialyzer and replaced with saline. If air is not removed from the dialyzer, the air can cause clotting and blockages in the hollow fibers of the dialyzer membrane which reduces the efficiency of the dialyzer during treatment. Air trapped in the dialyzer can reduce dialyzer clearance by preventing diffusion between the blood and dialysate compartments. Additionally, clots in the returned blood to the patient can lead to increased risk of thrombosis. Finally, technicians can introduce error and inconsistently perform the steps for priming.

Hence, there is a need for an a venous air capture chamber that can effectively separate air bubbles from blood without causing mixing of new air into the blood, coagulation or hemolysis due to high shear stress. There is a need for a venous air capture chamber capable of bidirectional flow, allowing a simplified priming process that avoids the need to invert or "flip" a dialyzer during a priming step. The systems and methods should simplify and automate priming and improve usability. There is also a need for a bidirectional drip chamber that automates system priming and minimizes the risk of wet fibers trapping air.

SUMMARY OF THE INVENTION

The first aspect of the invention relates to a venous air capture chamber. In any embodiment of the first aspect of the invention, the venous air capture chamber comprises a chamber body comprising a top portion and a bottom portion; a fluid inlet upwardly extending from the bottom portion of the chamber body towards the top portion of the chamber body to form a fluid inlet tube terminating in a first fluid inlet port and a second fluid inlet port; wherein the first fluid inlet port and the second fluid inlet port are disposed tangential to a circle plane formed by a center axis of the chamber body; wherein the first fluid inlet port and second fluid inlet port are opposedly positioned on the fluid inlet at an angle of about 180°; and a fluid outlet on the bottom portion of the chamber body.

In any embodiment of the first aspect of the invention, the first fluid inlet port and second fluid inlet port are positioned at about a 90° turn relative to a fluid flow of the tube.

In any embodiment of the first aspect of the invention, the fluid outlet includes a mesh filter forming a cylindrical taper having a decreasing diameter in an upwardly direction from the bottom of the chamber and terminates in a substantially planar surface.

In any embodiment of the first aspect of the invention, the chamber body is a substantially ovoid in shape.

In any embodiment of the first aspect of the invention, the chamber body comprises a small diameter cylinder portion and a large diameter cylinder portion; wherein the large diameter cylinder portion is positioned higher relative to the large diameter cylinder portion.

In any embodiment of the first aspect of the invention, the fluid inlet is positioned in the chamber body in the large diameter cylinder portion; and wherein the fluid outlet is positioned on a bottom of the small diameter cylinder portion.

In any embodiment of the first aspect of the invention, the chamber body has a height of between 9 and 13 cm.

In any embodiment of the first aspect of the invention, the small diameter cylinder portion is inwardly sloping from a top of the small diameter cylinder portion to the bottom of the small diameter cylinder portion.

In any embodiment of the first aspect of the invention, the small diameter cylinder portion has a height of between 3 and 7 cm.

In any embodiment of the first aspect of the invention, the large diameter cylinder portion has a height of between 4 and 8 cm.

In any embodiment of the first aspect of the invention, the venous air capture chamber comprises a spiral flow inducing shelf positioned inside the chamber body at the fluid inlet flush to a bottom portion of the fluid inlet port.

In any embodiment of the first aspect of the invention, the spiral flow inducing shelf is downwardly sloping.

In any embodiment of the first aspect of the invention, the venous air capture chamber comprises a cap covering the top portion of the chamber body.

In any embodiment of the first aspect of the invention, the cap comprises two ports.

Any of the features disclosed as being part of the first aspect of the invention can be included in the first aspect of the invention, either alone or in combination.

The second aspect of the invention is drawn to an extracorporeal flow path. In any embodiment of the second aspect of the invention, the extracorporeal flow path comprises a dialyzer comprising a blood side of the dialyzer and a dialysate side of the dialyzer; a blood inlet fluidly connected to the blood side of the dialyzer and a blood outlet fluidly connected to the blood side of the dialyzer; a blood pump; and the venous drip chamber of the first aspect of the invention positioned in a venous blood line fluidly connectable to the dialyzer and to a patient.

In any embodiment of the second aspect of the invention, the extracorporeal flow path comprises an arterial air capture chamber positioned in an arterial blood line fluidly connectable to the dialyzer and to a patient.

In any embodiment of the second aspect of the invention, the blood pump can be a non-pulsatile pump.

Any of the features disclosed as being part of the second aspect of the invention can be included in the second aspect of the invention, either alone or in combination.

The third aspect of the invention is drawn to method comprising the steps of: pumping blood through the extracorporeal flow path of the second aspect of the invention; and pumping dialysate through the dialysate side of the dialyzer; wherein the step of pumping blood through the extracorporeal flow path comprises controlling the blood pump to pump the blood at a blood flow rate of between 50 mL/min and 500 mL/min.

In any embodiment of the third aspect of the invention, the method includes the step of filling the venous air capture chamber to a specified filling level; wherein the specified filling level is based on the blood flow rate.

In any embodiment of the third aspect of the invention, the specified filling level is between 40% to 65% when the blood flow rate is between 50 mL/min and 200 mL/min; the specified filling level is between 50% to 75% when the blood flow rate is between 100 mL/min and 275 mL/min; the specified filling level is between 65% to 85% when the blood flow rate is between 275 mL/min and 500 mL/min; and the specified filling level is between 70% to 85% when the blood flow rate is 500 mL/min or greater.

In any embodiment of the third aspect of the invention, the blood flow rate is between 275 and 500 mL/min and the specified filling level is between 65% and 80%.

Any of the features disclosed as being part of the third aspect of the invention can be included in the third aspect of the invention, either alone or in combination.

The fourth aspect of the invention is drawn to a method for priming a dialyzer. In any embodiment of the fourth aspect of the invention, a physiologically compatible saline is pumped through the extracorporeal flow path of the second aspect of the invention, and further pumped through a dialysate side of the dialyzer.

Any of the features disclosed as being part of the fourth aspect of the invention can be included in any other aspect of the invention, either alone or in combination.

DETAILED DESCRIPTION OF THE INVENTION

Figure 1:
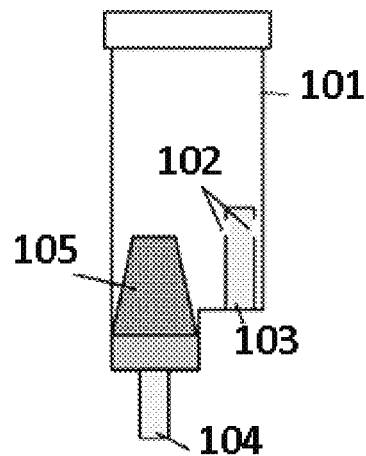
FIG. 1 is a generalized diagram of a venous air capture chamber.

Unless defined otherwise, all technical and scientific terms used herein generally have the same meaning as commonly understood by one of ordinary skill in the relevant art.

The articles "a" and "an" are used herein to refer to one or to more than one (i.e., to at least one) of the grammatical object of the article. By way of example, "an element" means one element or more than one element.

The term "about a 90° turn" refers to an angle defined by three points, wherein the angle is 90° or close to 90°.

The term "about 180°"' refers to an angle defined by three points, wherein the angle is 180° or close to 180°.

An "arterial air capture chamber" is a device placed in the arterial line of an extracorporeal flow path that separates and captures air mixed with the blood.

The term "arterial blood line" refers to a fluid line in an extracorporeal flow path that conveys blood from a patient to the dialyzer.

The term "blood flow rate" refers to the velocity of blood moving in a fluid line.

A "blood inlet" is a fluid connection through which blood can enter a component.

A "blood outlet" is a fluid connection through which blood can exit a component.

The term "blood pump" refers to a pump located in an extracorporeal flow path for pumping blood from a patient, to a dialyzer, and back to the patient.

The term "blood side of the dialyzer" refers to the portion of the dialyzer through which blood will travel during dialysis.

The terms "bottom portion" and "bottom section" refer to the portion of a component at a height lower than the center of a component when positioned for normal use.

A "cap" is a component that fits on top of a second component.

A "center axis" is an imaginary line through the center of a component from the top to the bottom of the component.

The term "chamber body" refers to the interior space of an air capture chamber.

The term "circle plane" refers to a horizontal plane that is substantially circularly shaped.

The term "comprising" includes, but is not limited to, whatever follows the word "comprising." Thus, use of the term indicates that the listed elements are required or mandatory but that other elements are optional and may or may not be present.

The term "consisting of" includes and is limited to whatever follows the phrase "consisting of" Thus, the phrase "consisting of" indicates that the limited elements are required or mandatory and that no other elements may be present.

The term "consisting essentially of" includes whatever follows the term "consisting essentially of" and additional elements, structures, acts or features that do not affect the basic operation of the apparatus, structure or method described.

The term "controlling the blood pump" or to "control the blood pump" refers setting a pump rate for a blood pump.

The term "cylindrical taper" refers to a three dimensional shape of a component that is substantially circular at a base of the component, and narrows towards a point at the top of the component.

The term "decreasing diameter" refers to a three dimensional shape of a component that becomes more narrow along from one end of the component towards the opposite end of the component.

The term "dialysate side of the dialyzer" refers to the portion of the dialyzer through which dialysate will travel during dialysis.

"Dialysis" is a type of filtration, or a process of selective diffusion through a membrane. Dialysis removes solutes of a specific range of molecular weights via diffusion through a membrane from a fluid to be dialyzed into a dialysate. During dialysis, a fluid to be dialyzed is passed over a filter membrane, while dialysate is passed over the other side of that membrane. Dissolved solutes are transported across the filter membrane by diffusion between the fluids. The dialysate is used to remove solutes from the fluid to be dialyzed. The dialysate can also provide enrichment to the other fluid.

The term "dialyzer" refers to a cartridge or container with two flow paths separated by semi-permeable membranes. One flow path is for blood and one flow path is for dialysate. The membranes can be in the form of hollow fibers, flat sheets, or spiral wound or other conventional forms known to those of skill in the art. Membranes can be selected from the following materials of polysulfone, polyethersulfone, poly(methyl methacrylate), modified cellulose, or other materials known to those skilled in the art.

The term "disposed" refers to a first components placement on a second component.

The term "downwardly sloping" refers to the configuration of a component wherein the component is at a higher elevation near an outer edge of a container or larger component, and at a lower elevation towards the center of the container or larger component.

The term "extracorporeal flow path" is the path through which blood will travel during dialysis.

The term "filling" or to "fill" refers to adding a fluid to a component or container.

The term "filling level" refers to the level of a fluid within a component.

The terms "fluidly connected," "fluidly connectable," and "fluid connection" refer to the ability of providing for the passage of fluid or gas from one point to another point. The two points can be within or between any one or more of compartments, modules, systems, components, and rechargers, all of any type.

The term "fluid flow of the tube" refers to a direction that fluid will move through a tube when used in normal operation.

A "fluid inlet" is a fluid connection through which a fluid can enter a component.

A "fluid inlet port" is an opening in a fluid inlet through which fluid enters a component.

A "fluid inlet tube" is a fluid connector through which a fluid can enter a component or container.

A "fluid outlet" is a fluid connection through which a fluid can exit a component.

The term "flush" refers to the position of a first component or structure relative to a second component or structure, wherein the first component or structure is in contact with the second component or structure.

The term "inner diameter" refers to the distance from the wall of a component, through the center of the component, and to the wall on the opposite side.

The term "inwardly sloping" refers to a configuration of a container wherein the container has a smaller diameter on either the top portion or the bottom portion than on the opposing portion.

A "large diameter cylinder portion" or "large cylinder portion" refers to the cylinder having a larger diameter in a component comprising at least two cylinders.

A "mesh filter" is a component made of interlaced or interconnected structures that provides openings between the structures.

The term "opposedly positioned" refers to the relative positions of two components wherein the two components are facing in substantially opposite directions.

A "patient" or "subject" is a member of any animal species, preferably a mammalian species, optionally a human. The subject can be an apparently healthy individual, an individual suffering from a disease, or an individual being treated for a disease.

A "physiologically compatible saline solution" is a solution that can be safely introduced into the bloodstream of a living person.

A "port" is an opening in a component through which fluid or gas may enter or leave the component.

The term "positioned" refers to the location of a particular component or structure.

The term "positioned higher" refers to the relative positions of two components wherein the component that is "positioned higher" is at a higher elevation when the system is in normal use.

"Priming" refers to preparing a system or component for use. In any embodiment, the term "priming" can refer to the process of pumping a liquid into a system, fluid lines, or other components to fill the system, fluid lines, or other components with the fluid.

The term "priming step" refers to a discrete action taken in order to prime a system.

The terms "pumping," "pumped," or to "pump" refers to moving a fluid, gas, or combination thereof, with a pump.

The term "small diameter cylinder portion" or "small cylinder portion" refers to the cylinder having a smaller diameter in a component comprising at least two cylinders.

The term "specified filling level" refers to a level of fluid within a component, such as a percentage of the component filled with fluid and is a predetermined level dependent upon other system parameters.

A "spiral flow-inducing shelf" refers to a shelf that causes fluid inside of the larger structure to move in a spiral flow path.

The term "substantially ovoid" refers to a component that has rounded ends and a slightly elongated shape.

The term "substantially planar surface" refers to an outer surface of a component that is generally a flat surface.

The term "tangential" or "tangentially" refers to a position of a first component on a second component, wherein the first component occupies a space within a horizontal plane of the second component.

The term "terminating" refers to an outer edge of a component or structure.

The term "top portion" refers to the portion of a component at a height higher than the center of a component when positioned for normal use.

The term "upwardly extending" refers to a configuration of a component wherein, during normal operation, the component is positioned from a bottom portion towards a top portion of a second component.

A "venous air capture chamber" is a device placed in the venous line of an extracorporeal flow path that separates and captures air mixed with the blood.

The term "venous blood line" refers to a fluid line in an extracorporeal flow path that conveys blood from a dialyzer to the patient.

Venous Air Capture Chamber

The invention relates to a venous air capture chamber for hemodialysis and a method for performing dialysis that minimizes contact or mixing between the blood and air. The air capture chamber can be adapted for disposable or non-disposable sets and provides for bidirectional flow during priming and blood return functions. Bidirectional flow during priming can be implemented in a compact portable hemodialysis system that does not require the dialyzer to be manually inverted during the priming process. The structural features of the venous air capture chamber minimize stagnant areas and avoid high shear stresses to inhibit blood coagulation or activation of thrombosis.

FIG. 1 illustrates a venous air capture chamber in accordance with the present invention. In any embodiment of the first, second, third, or fourth aspects of the invention, the venous air capture chamber can comprise a chamber body 101, a fluid inlet extending upwardly from a bottom portion towards a top portion of the chamber body 101 to form a fluid inlet tube 103, a fluid outlet 104 and an optional mesh filter 105 covering the fluid outlet 104. The mesh filter 105 can be a cone shape having a cylindrical taper wherein the diameter of the cone decreases in an upwardly direction towards a top of the chamber body 101. The cone shape can terminate in a substantially planar surface or a point. In some embodiments of the invention, the venous chamber does not comprise mesh filter 105. As described herein, the fluid inlet 103 can terminate in two fluid inlet ports 102 placed on the fluid inlet 103, the fluid inlet ports disposed tangential to a circle plane formed by a center axis of the chamber body 101. The two fluid inlet ports 102 can be a first fluid inlet port and second fluid inlet port that are positioned at about a 90° turn relative to a fluid flow of the tube or a vertical axis of the tube. In any embodiment of the first, second, third, or fourth aspects of the invention, the two fluid inlet ports 102 can be opposedly positioned on the fluid inlet tube 103 and spaced at an angle of about 180° apart, as shown in FIG. 1.

Figure 2A:
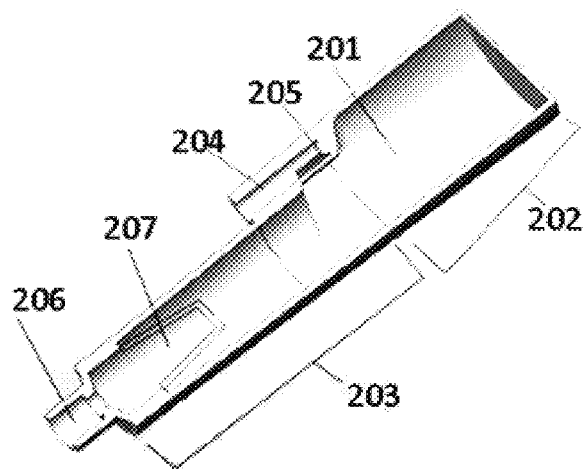
FIGS. 2a-b are detailed diagrams of a venous air capture chamber.

FIG. 2a illustrates a non-limiting embodiment of the venous air capture chambers described herein. In any embodiment of the first, second, third, or fourth aspects of the invention, the venous air capture chamber can comprise a chamber body 201. The chamber body can comprise two portions, a small diameter cylinder portion 203 and a large diameter cylinder portion 202, with the large diameter cylinder portion 202 positioned higher relative to the small diameter cylinder portion 203. The upwardly extending fluid inlet can form a fluid inlet tube 204 with fluid inlet ports 205. The fluid inlet tube 204 can enter the chamber body in the small diameter cylinder portion 202. The fluid outlet 206 can be placed on the bottom portion of the chamber body 201 and can comprise an optional mesh filter 207. The optional mesh filter 207 can be any type of mesh filter known in the art. The mesh filter 207 can have a cylindrical taper having a decreasing diameter in an upwardly direction from the bottom of the chamber body 201 and terminating in a substantially planar surface as illustrated in FIG. 2a.

Figure 2B:
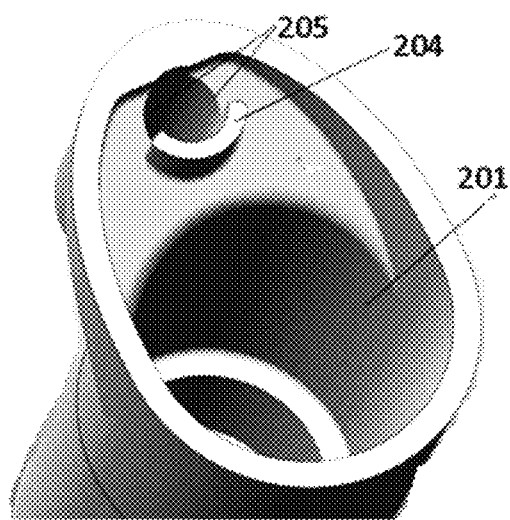

FIG. 2b illustrates a detailed view of the fluid inlet design. As shown in FIG. 2b, the fluid inlet tube 204 can comprise two opposedly positioned fluid inlet ports 205. The opposedly positioned fluid inlet ports 205 can be placed in a circle plane formed around the center axis of the chamber body 201. In any embodiment of the first, second, third, or fourth aspects of the invention, the fluid inlet ports 205 can be positioned at about 180° relative to the fluid inlet tube 204.

Figure 3A:
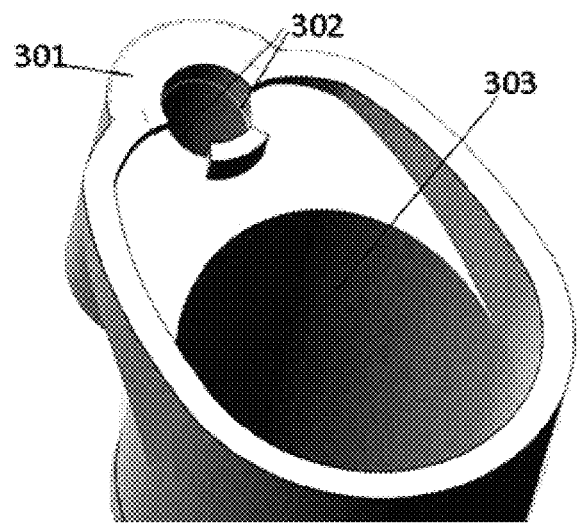
FIGS. 3a-b are detailed diagrams of fluid inlet designs for a venous air capture chamber.
Figure 3B:
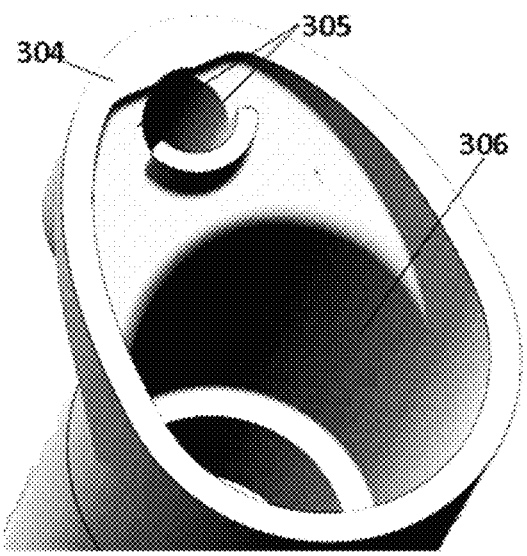

FIGS. 3a and 3b show variations of the fluid inlet design. As illustrated in FIG. 3a, the fluid inlet ports 302 can be located at a position close to an inner wall 301 of the chamber body and at a distance from the small diameter cylinder portion 303 with downwardly sloped surface to facilitate downward fluid flow. As illustrated in FIG. 3b, the fluid inlet ports 305 can alternatively be located closer to the small diameter cylinder portion 306 and further from the inner wall 304 of the chamber body. A downwardly sloped surface can have a rounded cliff edge and a steeper slope that shown in FIG. 3a to facilitate downward fluid flow. The sloped surface can also radiate outwards along an inner perimeter of the small diameter cylinder portion 303.

Figure 4A:
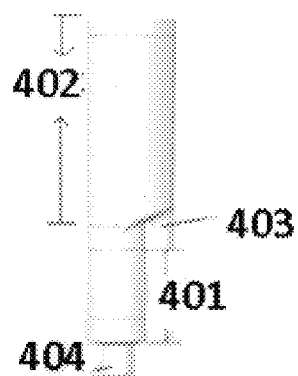
FIGS. 4a-b are detailed diagrams of venous air capture chamber bodies.
Figure 4B:
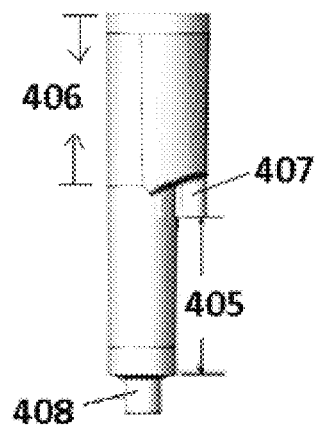

FIGS. 4a and 4b illustrate different embodiments of the chamber body. The embodiment shown in FIG. 4a provides a short small diameter cylinder portion 401 of the chamber body relative to the large diameter cylinder portion 402. The upwardly extending fluid inlet 403 enters at the large diameter cylinder portion 402. The fluid outlet 404 is at the bottom of the small diameter cylinder portion 401. FIG. 4b illustrates a similar venous air capture chamber with small diameter cylinder portion 405, a large diameter cylinder portion 406, a fluid inlet 407 and fluid outlet 408. In FIG. 4a the venous air capture chamber has shorter small diameter cylinder portion 401 relative to the large diameter cylinder portion 402 than the venous air capture chamber of FIG. 4b, which has a longer small diameter cylinder portion 405 relative to the large diameter cylinder portion 406. The height of the small cylinder portion of the venous air capture chamber can be set as any height, including between 3 and 7 cm. The large cylinder portion can be any height, including between 4 and 8 cm.

Figure 5A:
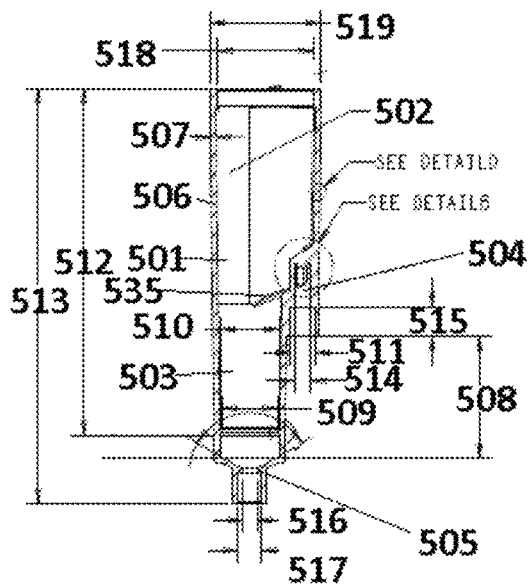
FIGS. 5a-5f show schematics of the venous air capture chamber.
Figure 5B:
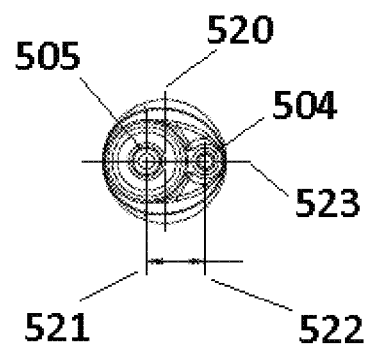
Figure 5C:
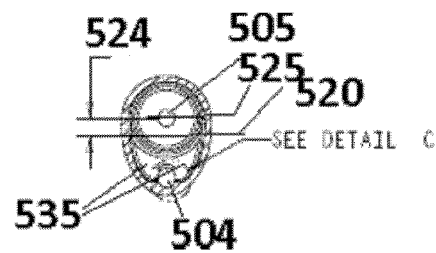

FIG. 5a-c show schematics of a non-limiting embodiment of the venous air capture chamber of the invention. As illustrated in FIG. 5a, the venous air capture chamber can, in any embodiment of the first, second, third, or fourth aspects of the invention, comprise a chamber body 501, an upwardly extending fluid inlet 504, and a fluid outlet 505 positioned on the bottom portion of the chamber body 501. As described, the chamber body 501 can comprise a large diameter cylinder portion 502 and a small diameter cylinder portion 503, with the large diameter cylinder portion 502 positioned higher relative to the small diameter cylinder portion 503.

In any embodiment of the first, second, third, or fourth aspects of the invention, the large diameter cylinder portion 502 can have a diameter of any size. In any embodiment of the first, second, third, or fourth aspects of the invention, the inner diameter 518 of the large diameter cylinder portion 502 can be set at any size between 1.8 and 4.0 cm. The outer diameter 519 of the large diameter cylinder portion 502 can be set at any size between 1.9 and 4.1 cm. In any embodiment of the first, second, third, or fourth aspects of the invention, the small diameter cylinder portion 503 can be inwardly sloping from the top of the small diameter cylinder portion 503 to the bottom of the small diameter cylinder portion 503. As such, near the top of the small diameter cylinder portion, the inner diameter of the small diameter cylinder portion 503 can be between of 1.2 and 2.0 cm, as denoted by diameter 510. At the bottom portion of the small diameter cylinder portion 503, the inner diameter can be between 1.1 and 1.9 cm, but smaller relative to the top of the small diameter cylinder portion 503, as shown by diameter 509. In any embodiment of the first, second or third aspects of the invention, the height of the small diameter cylinder portion 503 can be between 2.5 and 4.1 cm, shown as height 508.

In any embodiment of the first, second, third, or fourth aspects of the invention, the venous air capture chamber can have a total height of between 9 and 13 cm, shown by height 513. The venous air capture chamber can have a height measured from the top of the venous air capture chamber to the top of the fluid outlet 505 of between 8 and 11 cm, shown by height 512. In any embodiment of the first, second, third, or fourth aspects of the invention, the chamber wall 506 can have a thickness of between 0.1 and 0.3 cm as shown by width 507.

In any embodiment of the first, second, third, or fourth aspects of the invention, the fluid inlet 504 can form a fluid inlet tube. The fluid inlet tube can have a width of between 0.3 and 0.6 cm as shown by width 514. The chamber body can extend over the fluid inlet tube to a distance of between 0.6 and 1.0 cm from the chamber body 501, as shown by height 515. The fluid inlet 504 can have a diameter of between 0.35 and 0.8 cm over the fluid inlet tube, as shown by diameter 511. The fluid outlet 505 can form a fluid outlet tube with a restricted diameter of between 0.3 and 0.6 cm, as shown by diameter 516. The fluid outlet tube can have a total diameter of between 0.35 and 0.9 cm as shown by diameter 517.

In any embodiment of the first, second, third, or fourth aspects of the invention, a spiral flow inducing shelf 535 can be included in the venous air capture chamber. The spiral flow inducing shelf 535 is a feature that can help smooth fluid flow through the chamber and eliminate stagnant areas, particularly at low fluid flow rates. The spiral flow inducing shelf 535 can be downwardly sloping and have a rounded cliff edge to facilitate fluid flow. As illustrated in FIG. 5*a*, in any embodiment of the first, second, third, or fourth aspects of the invention, the spiral flow inducing shelf 535 can be positioned flush to the bottom portion of the fluid inlet 504 and can be downwardly sloping.

FIG. 5*b* shows a bottom view of the venous air capture chamber illustrated in FIG. 5*a*. Axis 520 is a center axis of the large diameter cylinder portion of the chamber body. Axis 521 is a center axis of the small diameter cylinder portion of the chamber body above fluid outlet 505. Fluid inlet 504 has a center axis 522. Axis 523 is an axis through the chamber body along a plane of the fluid inlet 504 and fluid outlet 505. In any embodiment of the first, second, third, or fourth aspects of the invention, the horizontal distance from the center axis 522 of the fluid inlet 504 to the center axis 521 of the small diameter cylinder portion of the chamber can be between 1.0 and 1.8 cm.

FIG. 5*c* is a different cross section of the venous drip chamber. As shown in FIG. 5*c*, the distance between a center axis 525 of the fluid outlet 505 to the center axis 520 of the large diameter cylinder portion of the chamber body can be between 0.3 and 0.6 cm, shown by width 524. The spiral flow inducing shelf 535 is shown flush to the bottom portion of the fluid inlet 504.

Figure 5D:
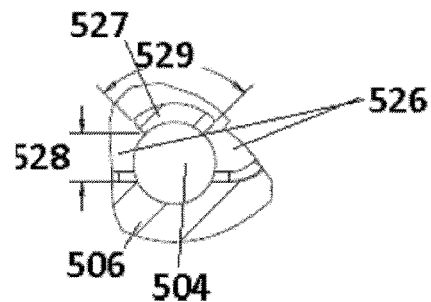

FIG. 5*d* shows a detailed view of the fluid inlet 504, labeled as Feature C in FIG. 5*c*. As described, the fluid inlet 504 can comprise two fluid inlet ports 526 with the two fluid inlet ports 526 opposedly positioned on the fluid inlet 504 at an angle of about 180° along the chamber wall 506. The opposedly positioned fluid inlet ports 526 are formed by fluid inlet tip 527, which separates the two fluid inlet ports 526. In any embodiment of the first, second, third, or fourth aspects of the invention, the fluid inlet port 526 can have a diameter of between 0.15 and 0.35 cm, shown by diameter 528. The width 528 of the fluid inlet ports will define the angle of the fluid inlet tip 527, which can be between 70° and 130°, shown as angle 529.

Figure 5E:
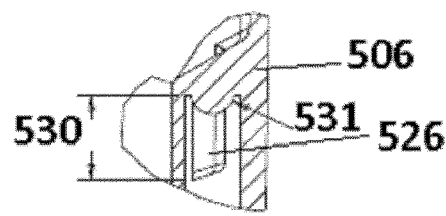

FIG. 5*e* illustrates the fluid inlet 504 entering the chamber body 501, shown as Detail B in FIG. 5*a*. As shown in FIG. 5*e*, each fluid inlet port 526 can have a height of between 0.50 and 1.0 cm, shown as height 530. In any embodiment, the top of the fluid inlet port 526 can be with the curved with the curve defining a circle with a radius of between 0.55 and 0.80 cm, shown by radius 531.

Figure 5F:
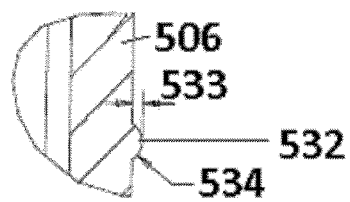

FIG. 5*f* is a close up of a feature in the chamber wall 506, shown as Detail D in FIG. 5*a*. The feature 532 is a protrusion in the chamber wall 506. The feature 532 can extend between 0.01 and 0.02 cm from the chamber wall 506, shown as width 533. The feature 532 can be rounded, defining a circle with a radius of between 0.04 and 0.06 cm, shown by radius 534.

Figure 6A:
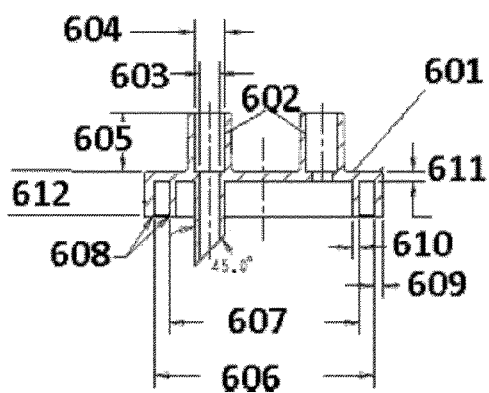
FIGS. 6a-b show schematics of a cap to be used on a venous air capture chamber.

FIG. 6*a* is a schematic of the cap portion 601 of the venous drip chamber. The cap 601 can comprise two ports 602. The ports 602 are used for both air in adjusting the chamber level and pressure monitoring, and for liquid in adding medications or physiologically compatible saline. Each port 602 can contain a tube with a diameter of between 0.15 and 0.4 cm, shown as diameter 603. The ports 602 can themselves have an inner diameter of between 0.3 and 0.5 cm, shown as diameter 604. Each port 602 can extend to a height of between 0.7 and 0.9 cm above the outer surface of the cap 601, shown as height 605. In order to fit over the top of the chamber body, the cap can have receiving slots 608 into which an edge of the chamber body can fit. The inner edges of the receiving slots 608 can define an inner diameter of between 1.8 and 4.0 cm, shown as diameter 607. The outer edges of the receiving slots 608 can define an inner diameter of between 2.2 and 4.4 cm, shown as diameter 606. The cap 601 can have a thickness on the inner edge of the receiving slot 608 of between 0.08 and 0.12 cm, shown as width 610, and a thickness of between 0.10 and 0.14 cm on the outer edge of the receiving slot 608, shown as width 609. The cap 601 can have a top thickness of between 0.1 and 0.3 cm, shown as height 611. A height from the base of the cap 601 to the bottom of the receiving slots 608 can be between 0.5 and 0.7 cm, shown as height 612.

Figure 6B:
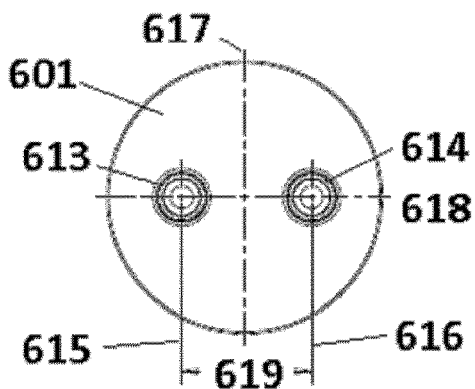

FIG. 6*b* is a schematic showing a top view of the cap 601. As described, the cap 601 can comprise a first port 613 and a second port 614, shown collectively as ports 602 in FIG. 6*a*. Each port 613 and 614 can have a center axis 615 and 616 respectively. The center axis 615 and 616 of each port 613 and 614 can be spaced evenly apart from a center axis 617 of the cap 601. Each of the ports 613 and 614 can be positioned on center axis 618 of the cap 601. A distance between the center axis 615 of port 613 and center axis 616 of port 614 can be between 1.0 and 2.0 cm.

Figure 7:
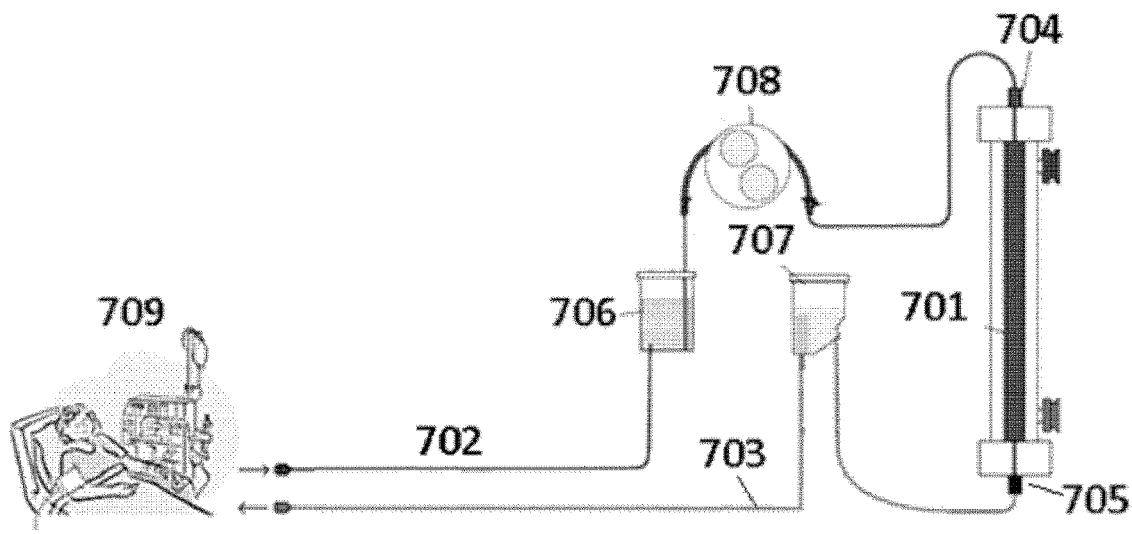
FIG. 7 is a diagram of an extracorporeal flow path.

In any embodiment of the first, second, third, or fourth aspects of the invention, as shown in FIG. 7, the venous air capture chambers can be used in an extracorporeal flow path for hemodialysis. The extracorporeal flow path can comprise a dialyzer 701. Blood from a patient 709 can be pumped through an arterial blood line 702, fluidly connected to dialyzer 701, and enter the dialyzer 701 through blood inlet 704. Blood can exit the dialyzer 701 through blood outlet 705, which is fluidly connected to venous blood line 703, and be pumped back to the patient 709. One of skill in the art will understand that the extracorporeal flow path depicted in FIG. 7 is for illustrative purposes only, and that additional components, sensors, lines and pumps can be included. Blood pump 708 can be used to pump the blood through the extracorporeal circuit. Blood in the arterial blood line 702 can be pumped through arterial air capture chamber 706 as described herein. The arterial air capture chamber 706 can be placed at any location in the arterial line 702, including either upstream or downstream of blood pump 708. The venous blood line 703 can also comprise the venous air capture chamber 707. The blood, upon entering the dialyzer 701 can enter a blood side of the dialyzer 701. The dialyzer 701 can also comprise a dialysate side of the dialyzer 701 separated from the blood side by a semi-permeable membrane. Solutes in the blood can pass through the semi-permeable membrane and enter the dialysate where the solutes can be removed or the dialysate discarded. One of skill in the art will understand that the fluid flow rates in relation to the experiments described herein are equivalent to blood flow rates through the extracorporeal flow path. In use, a user can control the blood pump 708 to achieve a combination of blood flow rate and filling level as described to allow the venous air capture chamber 707 to capture air while avoiding stagnant flow or overly high shear stress. The blood pump 708 can be any type of pump used in the art.

In addition to the advantageous results with respect to residence time, shear stress, and air capture described herein, the venous air capture chambers described herein advantageously allow for bidirectional fluid flow through the chamber body. The bidirectional fluid flow functionality allows for a simplified priming process, without the need to flip the dialyzer for priming of the fluid lines. The venous air capture chambers described herein can be constructed from any material known in the art, including but not limited polyvinyl chloride (PVC) and polycarbonate (PC).

Figure 55A:
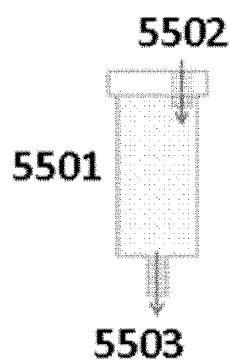
FIGS. 55*a-b* illustrate a comparison of a conventional venous air capture chamber and the present venous air capture chamber.
Figure 55B:
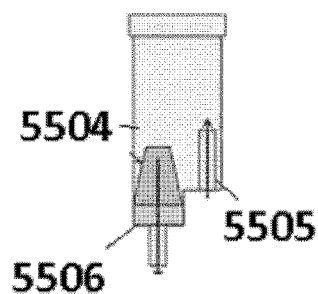

FIGS. 55a-b illustrate the differences between the present venous air capture chamber and conventional air capture chambers. As shown in FIG. 55a, a conventional venous air capture chamber 5501 has a fluid inlet 5502 at the top of the air capture chamber 5501, and a fluid outlet 5503 at the bottom of the air capture chamber 5501. Because fluid cannot travel from the fluid outlet 5503 to the fluid inlet 5502, the conventional venous air capture chamber 5501 cannot allow for bidirectional flow. In contrast, as shown in FIG. 55b, the venous air capture chamber 5504 has a fluid inlet 5505 and a fluid outlet 5506 that are both positioned on the bottom portion of the venous air capture chamber 5504. As such, fluid is capable of moving from the fluid outlet 5506 to the fluid inlet 5505, allowing for fluid to move bi-directionally through the venous air capture chamber 5504.

Figure 56A:
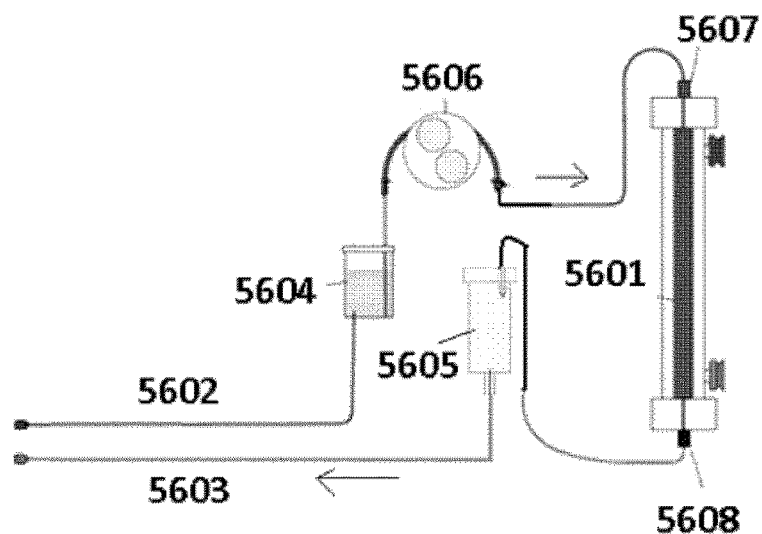
FIGS. 56*a-c* show extracorporeal flow paths set up for dialysis and priming using both conventional and bi-directional air capture chambers.

As described, the venous air capture chamber of the present invention advantageously allows for bidirectional flow through the venous air capture chamber, simplifying the process of priming the dialysis system. In any embodiment of the first, second or third aspects of the invention, the arterial air capture chambers used in the extracorporeal flow path can also allow for bidirectional flow. FIG. 56a shows a traditional extracorporeal flow path configured for use in dialysis. Blood from a patient travels to a dialyzer 5601 through arterial blood line 5602, entering at blood inlet 5607, as shown by the arrow on the arterial blood line 5602 in FIG. 56a. Blood from the dialyzer 5601 exits through blood outlet 5608, and travels back to the patient through venous blood line 5603, as shown by the arrow on the venous blood line 5603. An arterial air capture chamber 5604 is placed in the arterial blood line 5602 in order to remove air from the blood before reaching the dialyzer 5601. A venous air capture chamber 5605 is placed in the venous blood line 5603 in order to remove air from the blood before being returned to the patient. Blood pump 5606 provides the driving force to move blood through the extracorporeal flow path.

Figure 56B:
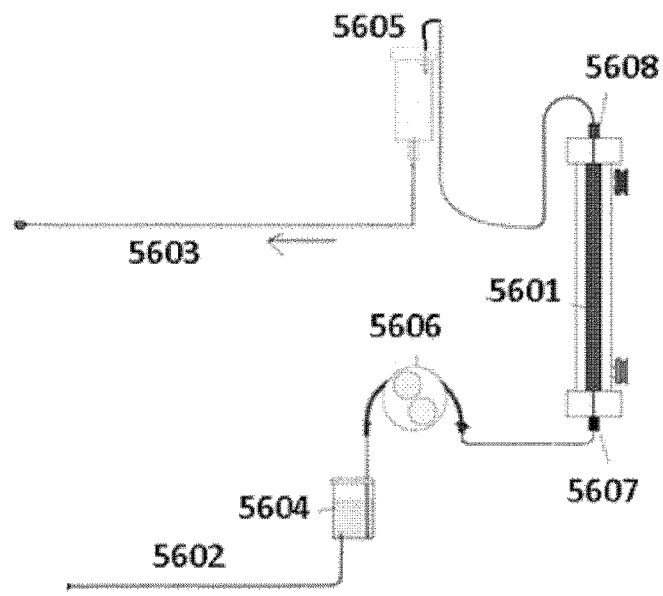

FIG. 56b shows an extracorporeal flow path set up for priming of the system. Due to gravity, in order to prime the dialyzer 5601 and extracorporeal flow path, physiologically compatible saline must be pumped through the dialyzer 5601 from the bottom of the dialyzer 5601 to the top of the dialyzer 5601 in order to push air out of the dialyzer 5601 from the top. The priming process requires fluid to move through the extracorporeal flow path in the opposite direction as in normal use. Because conventional air capture chambers do not allow for bidirectional fluid flow, the direction of fluid flow through the extracorporeal flow path cannot be simply reversed. Instead, the entire dialyzer and extracorporeal flow path must be flipped in order to allow fluid and air to move from the top of the dialyzer 5601, through the blood outlet 5608 and into the venous line 5603 through the venous air capture chamber 5605, which after being flipped is connected to the top of the dialyzer 5601, as shown by the arrow on venous line 5603 in FIG. 56b.

Figure 56C:
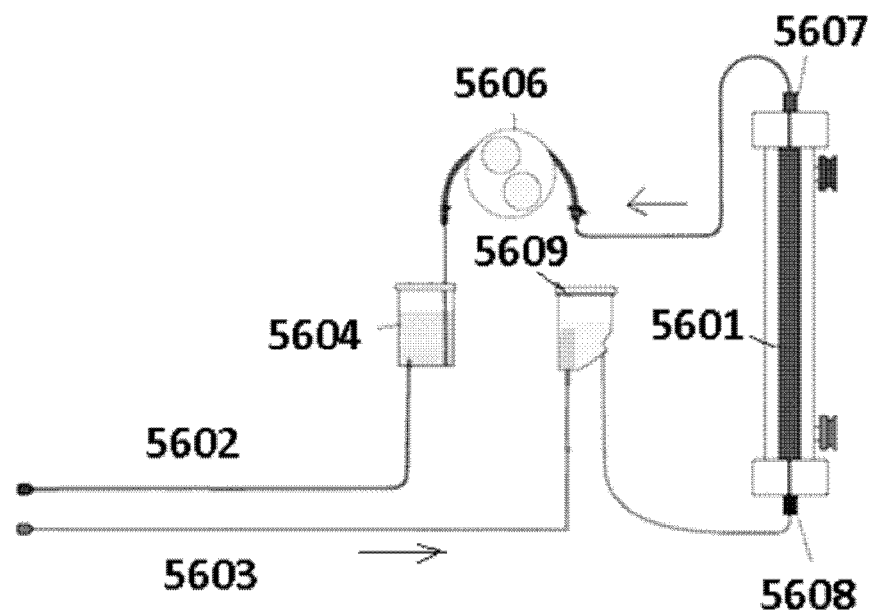

FIG. 56c shows an extracorporeal flow path using the bidirectional air capture chambers of the present invention. Advantageously, because the arterial air capture chamber 5604 and the venous air capture chamber 5609 of the present invention allows for bidirectional flow, the system can be primed without the need to flip the dialyzer 5601. Because fluid can flow in through the fluid outlet of the arterial air capture chamber 5604, and can flow out of the fluid inlet of arterial air capture chamber 5604, and because fluid can flow in through the fluid outlet of venous air capture chamber 5609 and out through the inlet of venous air capture chamber 5609, the direction of fluid flow in the extracorporeal flow path can be reversed, and fluid and air can be removed from the top of the dialyzer 5601 simply by changing the direction of blood pump 5606, as shown by the arrow on arterial blood line 5602 and venous blood line 5603 in FIG. 56c.

Figure 57:
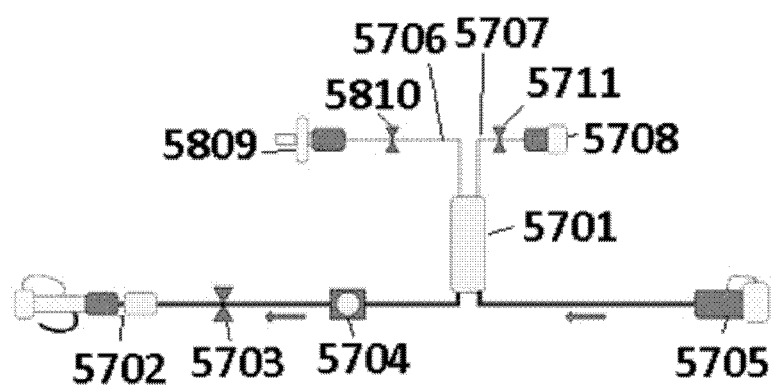
FIG. 57 shows a detailed view of a venous blood line.

FIG. 57 is a detailed view of a non-limiting venous blood line set up that can be used with the venous air capture chambers described herein. The venous blood line can comprise a venous air capture chamber 5701 as described herein. The venous blood line can be connected to a patient through luer connector 5702, and can be connected to a dialyzer outlet through dialyzer connector 5705. In any embodiment of the first, second, third, or fourth aspects of the invention, the luer connector 5702 can optionally include a recirculation connector, which allows recirculation of fluid through the entire extracorporeal flow path. Line clamp 5703 can be used to restrict or stop blood flow if necessary through the venous blood line. A sample port 5704 can be included in the venous blood line for blood sampling. As described, the venous air capture chamber 5701 can comprise a cap with two ports comprising line 5706 and line 5707 for removal of captured air, adjustment of the filling level, monitoring of pressure, or addition of medications. Each of the lines 5706 and 5707 can terminate in luer connectors 5709 and 5708, respectively. Line clamp 5710 in line 5706 and line clamp 5711 in line 5707 can be used to control the movement of air or fluids through the lines.

Figure 8:
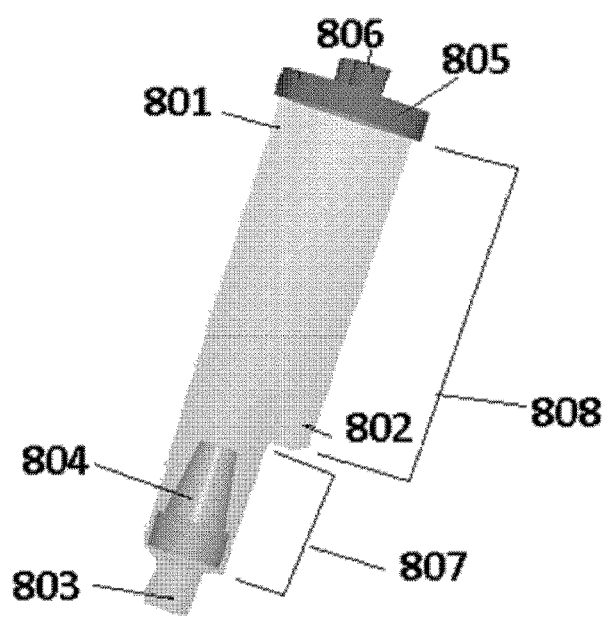
FIG. 8 shows a computer aided design picture of a venous air capture chamber.

FIG. 8 illustrates a computer aided design of a venous air capture chamber in accordance with the present invention. As described, in any embodiment of the first, second, third, or fourth aspects of the invention, the venous air capture chamber can comprise a chamber body 801, a fluid inlet 802, a fluid outlet 803, and a mesh filter 804. The venous air capture chamber can also comprise a cap 805 covering the top portion of the chamber body 801. The cap 805 can comprise one or more ports 806 for removal of air captured by the chamber, measuring pressure in the chamber, or adding or removing liquid. As described herein, the chamber body 801 can comprise two cylinder portions, a small diameter cylinder portion 807, and a large diameter cylinder portion 808. The large diameter cylinder portion 808 can be positioned higher relative to the small diameter cylinder portion 807, with the fluid outlet 803 placed at the bottom of the small diameter cylinder portion 807. In any embodiment of the first, second, third, or fourth aspects of the invention, the fluid inlet 802 can enter the chamber body 801 in the large diameter cylinder portion 808.

Based on computational flow monitoring described herein, a venous air capture chamber was constructed comprising a chamber body, an upwardly extending fluid inlet terminating in two fluid inlet ports opposely positioned on the fluid inlet tangential to a circle plane formed by a center axis of the chamber body at an angel of about 180° and a fluid outlet comprising a mesh filter. In order to determine the effects of each of the disclosed features of the venous air capture chamber on the flow of fluid through the venous air capture chamber, computational flow dynamic (CFD) analysis was conducted on several configurations of an venous air capture chamber as outlined herein. The CFD analysis simulated several configurations of the venous air capture chambers in order to optimize for geometry and filling levels. In order to carry out the CFD analysis, computer aided design models of the venous air capture chambers were created, similar to the model shown in FIG. 9. The CFD analysis was conducted with the assumption of Multi-phases (air and blood) and viscous laminar flow. The blood analogue used had a density 1044 kg/m$^3$ and viscosity 0.00271 PaS. Flow domain was based on the chamber inner surfaces, and inlet and outlet ports were created through ANSYS Fluent. The initial and boundary conditions used were steady, and chamber filling was not considered. The inlet velocity was calculated based on flow rate and inlet tubing section area (ID 4.5 mm and area 15.89 mm$^2$) and specified for the inlet port. The inlet velocities used in the experiments described herein were 0.104 m/s (100 ml/min), 0.288 m/s (275 ml/min), and 0.52 m/s (500 ml/min). The chamber volume was specified as the filling level of fluid by using ANSYS's region adaption/patch tools. Simulations were carried out both with and without the mesh filter. When considering the mesh filter, the filter was treated as a porous cell zone during the simulation. The original figures for the CFD analysis were in color. In order to better distinguish the diagrams, certain portions are shown with lead lines indicating the colors and relative velocities from the original figures Experiment 1

Figure 9A:
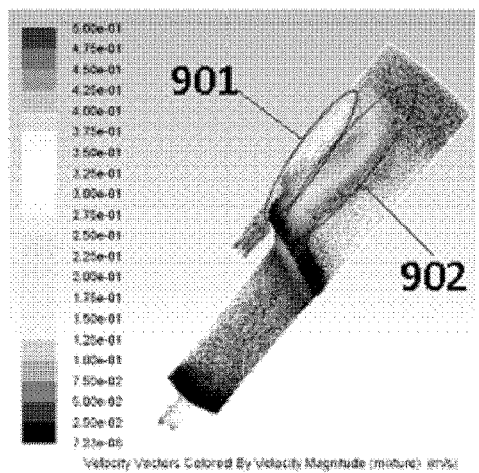
FIGS. 9a-b show velocity distribution vector diagrams for air capture chambers with differing body shapes.
Figure 9B:
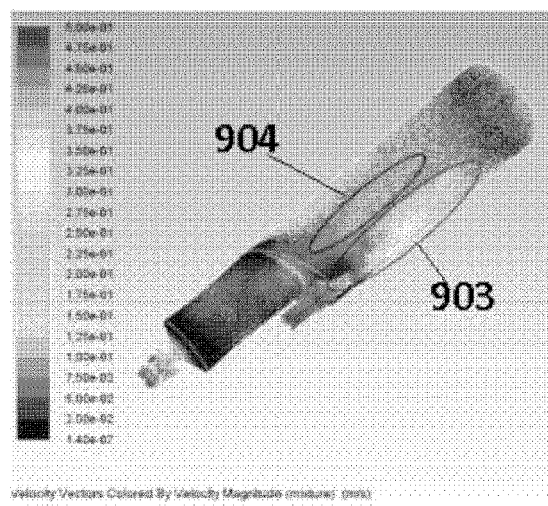

FIGS. 9a and 9b illustrate velocity vector distribution diagrams for venous air capture chambers with differing body shapes. Both the venous air capture chambers illustrated in FIGS. 9a and 9b have a flat inlet port design, with the fluid inlet port positioned on the top of the upwardly extending fluid inlet. The venous air capture chamber in FIG. 9a has a substantially circular body, while the venous air capture chamber in FIG. 10b has a substantially ovoid shaped body. The chambers in each of FIGS. 9a and 9b lack a mesh filter. The legend for FIGS. 9a and 9b transitions from a high velocity flow in red, to orange, to yellow, to green, to light blue, and then to blue. The same color transition applies for each flow diagram of the present invention. For example, FIG. 9b shows a high velocity flow in red at 5.00e-01 m/s, orange at 4.13e-01 m/s, yellow at 3.38e-01 m/s, green at 2.38e-01 m/s to light blue at 1.38e-01 m/s to a low velocity flow shown in blue at 1.40e-07.

As illustrated in FIG. 9aa, fluid flows straight upward from a flat inlet port in high velocity green area 901, before traveling downward through lower velocity light blue area 902. As illustrated in FIG. 9b, fluid flows straight upward from the flat inlet port in high velocity green area 903, before traveling downward through lower velocity light blue area 904. In each case, the flat inlet port creates a strong upward flow jet, and causes the fluid-air interface to be unstable, and a possibly causes a turbulent flow in the interface. The height which the flow jet can reach is dependent on the flow rate, which can make maintaining the fluid-air interface stable without turbulent flow at the fluid-air interface difficult. Further, the flow jet formation is dependent on the inlet port design, and not the body shape, as the upward flow is present in both of FIGS. 9a and 9b. An additional experiment showed that the same flat fluid inlet port provides the same upward flow stream in a chamber body that has a parallel cylinder shape. Based on the analysis in Experiment 1, a flat fluid inlet port provides an undesired upward flow stream.

Experiment 2

Figure 10A:
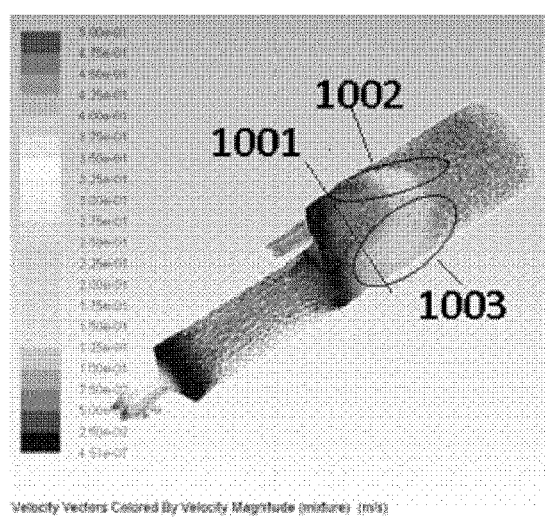
FIGS. 10a-b show velocity distribution vector diagrams for an air capture chamber with a substantially circular body shape.
Figure 10B:
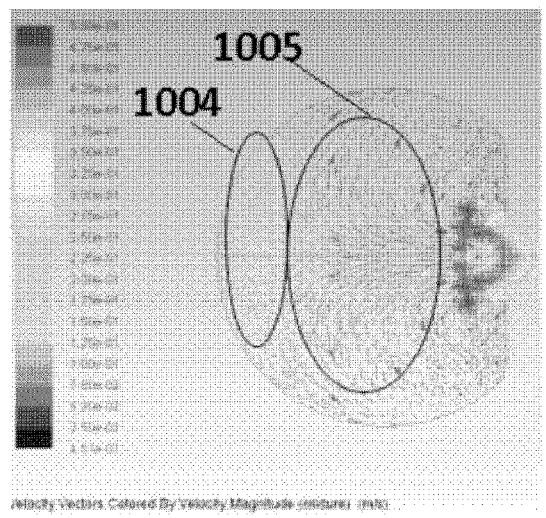
Figure 11A:
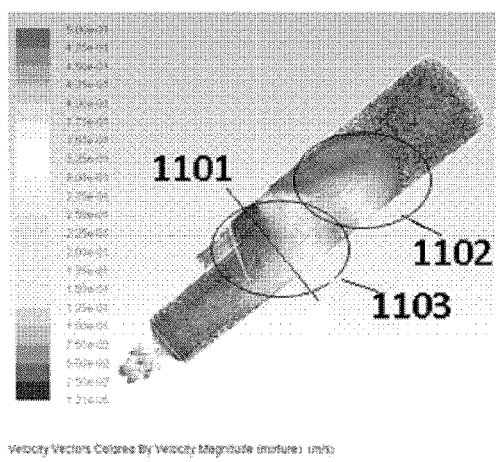
FIGS. 11a-b show velocity distribution vector diagrams for an air capture chamber with a substantially ovoid body shape.
Figure 11B:
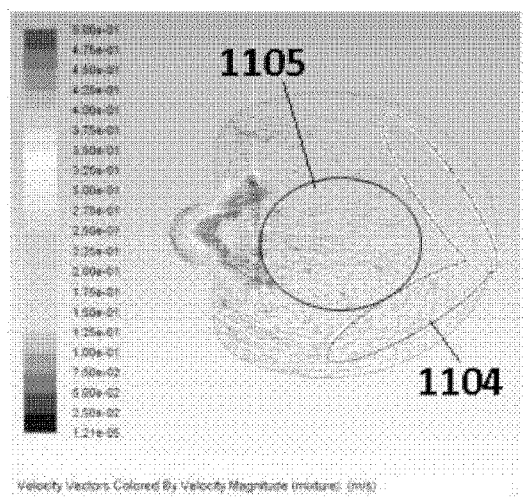
Figure 12A:
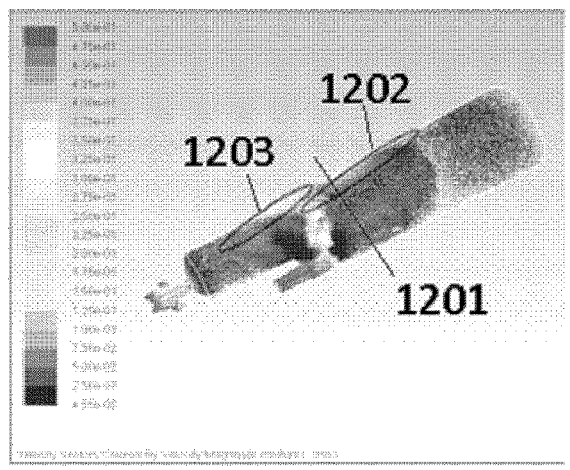
FIGS. 12a-b show velocity distribution vector diagrams for an air capture chamber with a parallel cylinder body shape.
Figure 12B:
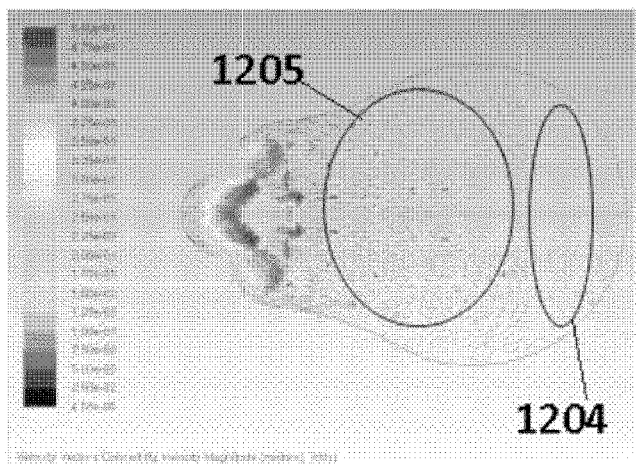

Velocity distribution vector diagrams were also created for chambers with an upwardly extending fluid inlet terminating in a fluid inlet port positioned at about a 90° turn relative to a fluid flow of the fluid inlet tube and disposed tangential to a circle plane formed by the center axis of the chamber body, and are shown in FIGS. 10-12. Each of the venous air capture chambers illustrated in FIGS. 10-12 lack a mesh filter. FIGS. 10a and 10b illustrate velocity distribution vectors for a venous air capture having a substantially circular shape. The legend for FIGS. 10a and 10b transitions from a high velocity flow in red at 5.00e-01 m/s, orange at 4.13e-01 m/s, yellow at 3.38e-01 m/s, green at 2.38e-01 m/s to light blue at 1.38e-01 m/s to a low velocity flow shown in blue at 4.51e-07. FIGS. 11a and 11b illustrate velocity distribution vectors for a venous air capture having a substantially ovoid shape. The legend for FIGS. 11a and 11b transitions from a high velocity flow in red at 5.00e-01 m/s, orange at 3.63e-01 m/s, yellow at 3.38e-01 m/s, green at 2.38e-01 m/s to light blue at 1.38e-01 m/s to a low velocity flow shown in blue at 1.21e-05. FIGS. 12a and 12b illustrate velocity distribution vectors for a venous air capture having a parallel cylinder body shape. The legend for FIGS. 12a and 12b transitions from a high velocity flow in red at 5.00e-01 m/s, orange at 4.13e-01 m/s, yellow at 3.38e-01 m/s, green at 2.38e-01 m/s to light blue at 1.38e-01 m/s to a low velocity flow shown in blue at 4.55e-05. FIG. 10b is a cross-sectional view of the chamber in FIG. 10a, taken at line 1101. FIG. 11b is a cross-sectional view of the chamber in FIG. 11a, taken at line 1201. FIG. 12b is a cross-sectional view of the chamber in FIG. 12a, taken at line 1301.

As illustrated in FIG. 10a, the fluid forms a single jet, which enters the air capture chamber in high velocity green area 1002, before slowing slightly and turning downward into the chamber body in lower velocity light blue area 1003. As illustrated in FIG. 10b, the downward moving fluid has a higher velocity near the chamber wall opposite the fluid inlet, shown as light blue area 1004, and a lower velocity through the center of the chamber body, shown as blue area 1005. As illustrated in FIG. 11a, fluid flows out from inlet port, hits the chamber wall, and splits into two flows, one is an upward flow and another is a downward flow in high velocity light blue areas 1102 and 1103. As illustrated in FIG. 11b, the downward moving fluid has a higher velocity near the chamber wall opposite the fluid inlet, shown as light blue area 1104, and a lower velocity through the center of the chamber body, shown as blue area 1105. The flow illustrated in FIGS. 11a and 11b is different from the flow illustrated in FIGS. 10a and 10b, and may be due to the fact that the substantially ovoid body in FIGS. 11a and 11b gives fluid less space to flow than the round body illustrated in FIGS. 10a and 10b, causing the split fluid flow. The upward flow stream in FIG. 11a may cause the fluid level to be unstable, while downward flow stream may bring bubbles into outlet port. As shown in FIGS. 12a and 12ba, the fluid also forms two flow streams, shown as higher velocity light blue areas 1202 and 1203. As illustrated in FIG. 12b, the downward moving fluid has a higher velocity near the chamber wall opposite the fluid inlet, shown as light blue area 1204, and a lower velocity through the center of the chamber body, shown as blue area 1205. The split fluid flow streams illustrated in FIGS. 12a and 12b may cause an unstable fluid level and bubbles in the outlet port, and may also be due to the fact that the parallel cylinder design provides less room for fluid to flow than the circular design in FIGS. 10a and 10b.

Based on the analysis in Experiment 2, a fluid inlet port positioned at about a 90° turn relative to a fluid flow of the fluid inlet tube and disposed tangential to a circle plane formed by the center axis of the chamber body provides strong downward flow in a round chamber, and provides split flows in ovoid or parallel cylinder shaped chamber bodies.

Experiment 3

Figure 13A:
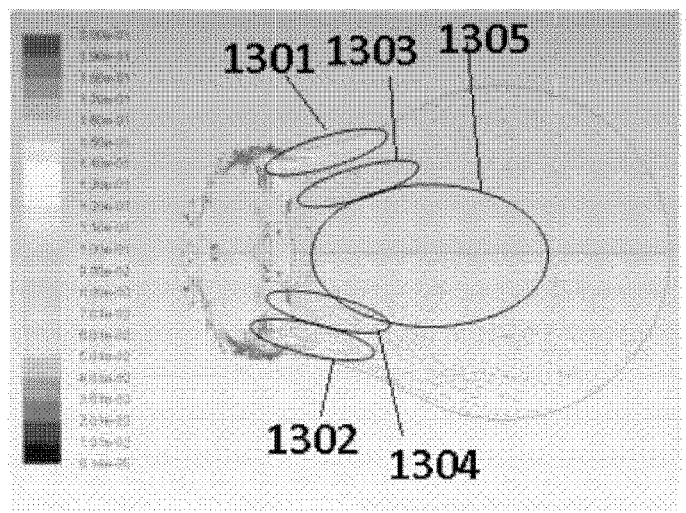
FIGS. 13a-b show velocity distribution vector diagrams for an air capture chamber with a two opposedly positioned fluid inlets and differing body shapes.
Figure 13B:
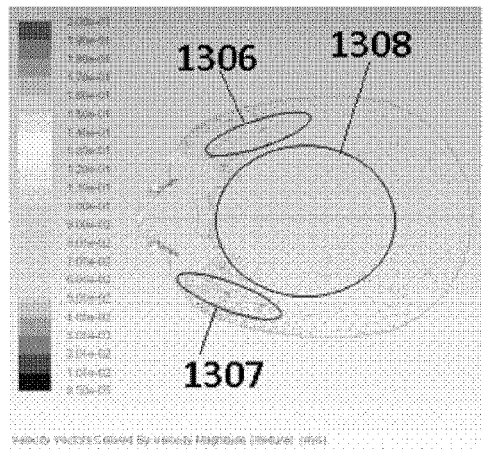

FIGS. 13a and 13b illustrate velocity distribution vectors for venous air capture chambers having an upwardly extending fluid inlet tube comprising two opposedly positioned fluid inlet ports placed in a circle plane formed around the center axis of the chamber body and at about 180° relative to the fluid inlet tube, as illustrated in FIG. 2. FIG. 13a illustrates the velocity distribution vectors for a chamber body having a parallel cylinder shape, while FIG. 13b illustrates the velocity distribution vectors for a chamber body having a substantially ovoid shape. The legend for FIGS. 13a and 13b transitions from a high velocity flow in red at 2.00e-01 m/s, orange at 1.65e-01 m/s, yellow at 1.35e-01 m/s, green at 8.50e-02 m/s to light blue at 4.50e-02 m/s to a low velocity flow shown in blue at 8.50e-05.

As illustrated in FIG. 13a, the fluid flow out of the fluid inlet port is extremely restricted by the wall of the chamber body, causing non-uniform flow. The fluid has a high velocity near the side of the chamber in red areas 1301 and 1302, a moderate velocity through the center of the chamber in green area 1305, and a low velocity in the blue areas labeled 1303 and 1304. In FIG. 13b, in contrast, the fluid flow around the fluid inlet port is more smooth and uniform, with a higher velocity through the center of the chamber in green area 1308, and a slightly lower velocity near the sides of the chamber in light blue areas 1306 and 1307.

Experiment 4

Figure 14A:
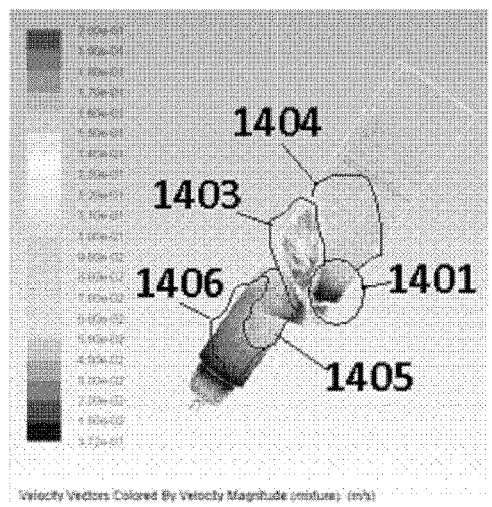
FIGS. 14a-b show velocity distribution vector diagrams for an air capture chamber with a two opposedly positioned fluid inlets and differing positions of the fluid inlets.
Figure 14B:
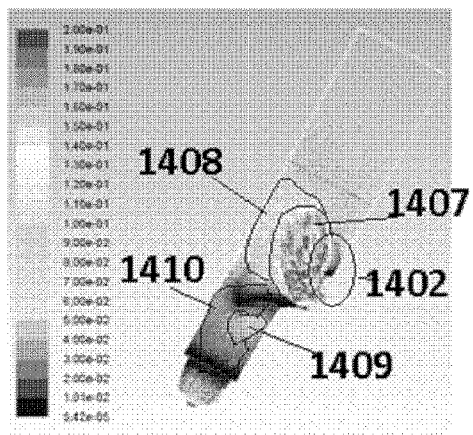

As described with reference to FIG. 3, the fluid inlet ports can be located at a position close to an inner wall of the chamber body and at a distance from the small diameter cylinder portion as illustrated in FIG. 3a the fluid inlet ports can be located closer to the small diameter cylinder portion as illustrated in FIG. 3b. FIG. 14a illustrates a velocity vector distribution diagram for a chamber body having an upwardly extending fluid inlet tube comprising two opposedly positioned fluid inlet ports placed in a circle plane formed around the center axis of the chamber body and at about 180° relative to the fluid inlet tube wherein the fluid inlet ports are located closer to a center of the small diameter cylinder; and FIG. 14b illustrates a velocity flow diagram for a similar chamber with the fluid inlet ports located closer to the wall of the chamber body. The legend for FIGS. 14a and 14b transitions from a high velocity flow in red at 2.00e-01 m/s, orange at 1.65e-01 m/s, yellow at 1.35e-01 m/s, green at 8.50e-02 m/s to light blue at 4.50e-02 m/s to a low velocity flow shown in blue at 5.42e-05 m/s.

FIG. 14a illustrates the fluid in red area 1403, green area 1404, light blue area 1405 and blue area 1406. FIG. 14b illustrates the fluid in red area 1407, green area 1408, light blue area 1409, and blue area 1410. As shown in FIG. 14a, the embodiment with the fluid inlet ports positioned closer to the center of the small diameter cylinder provides a large area of low velocity flow, illustrated in circle 1401. The low velocity area may lead to stagnant flow within the chamber body. As illustrated in FIG. 14b, there is a significantly smaller area of low velocity flow, illustrated in circle 1402, which provides advantageous fluid flow through the chamber.

Experiment 5

Figure 15A:
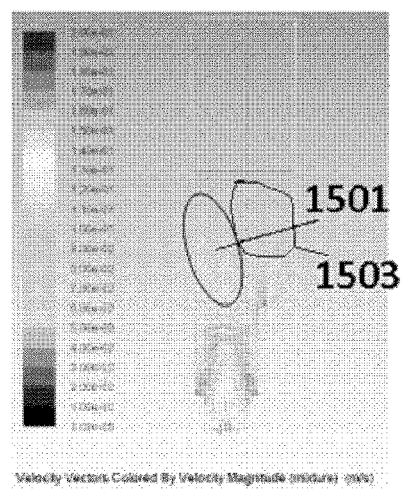
FIGS. 15a-b show velocity distribution vector diagrams for an air capture chamber with a two opposedly positioned fluid inlets and differing relative sizes of the small diameter cylinder and large diameter cylinder portions.
Figure 15B:
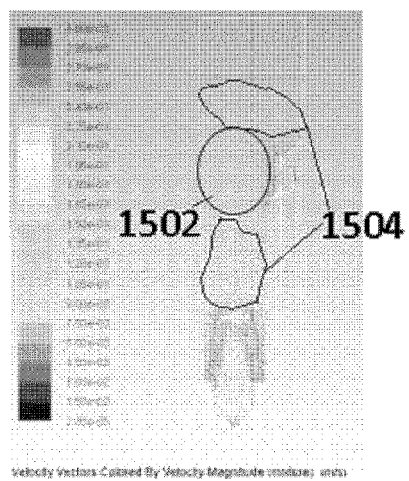

As noted with respect to FIGS. 4a and 4b, the small diameter cylinder portion of the chamber body may be constructed either as a short small diameter cylinder portion as in FIG. 4a or a long small diameter cylinder portion as in FIG. 4b. FIG. 15a illustrates a velocity distribution vector diagram for a venous air capture chamber having an upwardly extending fluid inlet tube comprising two opposedly positioned fluid inlet ports placed in a circle plane formed around the center axis of the chamber body and at about 180° relative to the fluid inlet tube, with a short small diameter cylinder portion relative to the large diameter cylinder portion. FIG. 15b illustrates velocity distribution vectors for the same venous air capture chamber with a long small diameter cylinder portion relative to the large diameter cylinder portion. The legend for FIG. 15a transitions from a high velocity flow in red at 2.00e-01 m/s, orange at 1.65e-01 m/s, yellow at 1.35e-01 m/s, green at 8.50e-02 m/s to light blue at 4.50e-02 m/s to a low velocity flow shown in blue at 3.09e-05 m/s. The legend for FIG. 15b transitions from a high velocity flow in red at 3.00e-01 m/s, orange at 2.48e-01 m/s, yellow at 2.03e-01 m/s, green at 1.48e-01 m/s to light blue at 6.75e-02 m/s to a low velocity flow shown in blue at 2.86e-05 m/s.

As illustrated in FIG. 15a, the short small diameter cylinder portion results in a non-uniform velocity distribution with a strong flow of about 0.13 to 0.14 m/s in the yellow area labeled 1501, and lower velocity in blue area 1503. In contrast, the long small diameter cylinder portion shown in FIG. 16b result in a more uniform flow velocity and a significantly less strong flow of about 0.03 to 0.06 m/s in the green area labeled 1502, with lower velocity in blue areas 1504. A uniform flow with a low velocity within the small diameter cylinder portion of the venous air capture chamber is helpful to allow bubbles to be capture prior to entering the fluid outlet.

Experiment 6

Figure 16A:
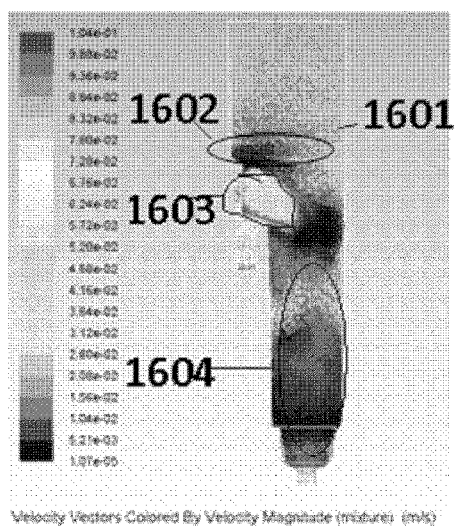
FIGS. 16a-d show velocity distribution vectors with a 60% filling level and an inlet velocity of 0.104 m/s.
Figure 16B:
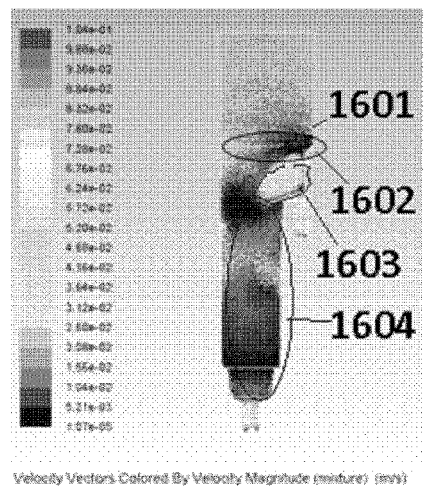
Figure 16C:
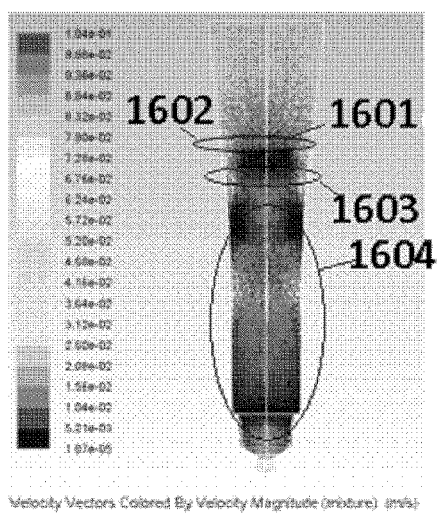
Figure 16D:
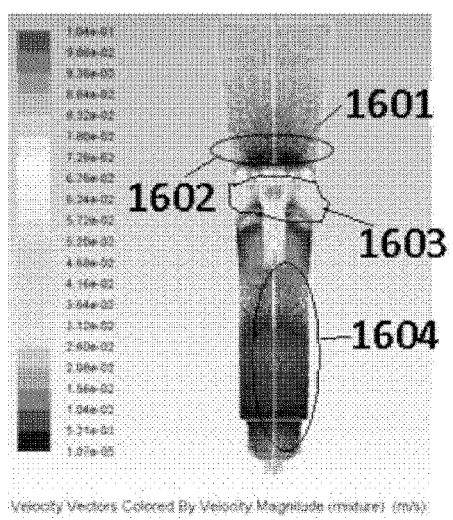
Figure 17:
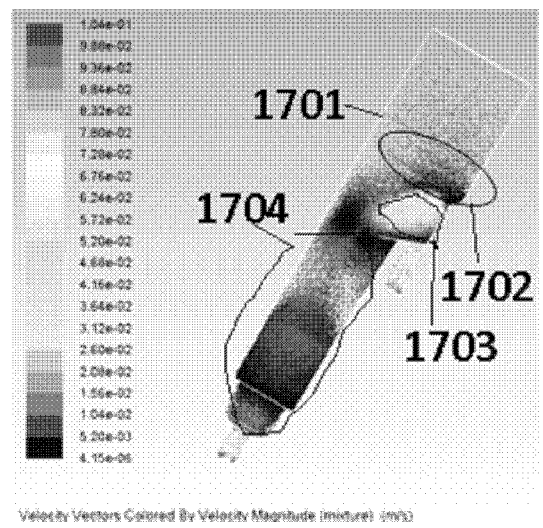
FIG. 17 shows a velocity distribution vector with a 65% filling level and an inlet velocity of 0.104 m/s.

Based on the analysis conducted in Experiments 1-5, a venous air capture chamber was selected for further analysis having an upwardly extending fluid inlet tube comprising two opposedly positioned fluid inlet ports placed in a circle plane formed around the center axis of the chamber body and at about 180° relative to the fluid inlet tube, a long small diameter cylinder portion, and a substantially ovoid shaped body and a mesh filter on the fluid outlet, and used in each of Experiments 6-8. FIGS. 16a-d illustrate velocity distribution vectors for such a venous air capture chamber at the conditions of a 60% filling level and 0.104 m/s inlet velocity, corresponding to a flow rate of 100 mL/min. FIG. 16a illustrates a front view of the chamber body, FIG. 16b illustrates a back view of the chamber body, FIG. 16c illustrates a right side view of the chamber body, and FIG. 16d illustrates a left-side view of the chamber body. In each of FIGS. 16a-d, the line 1601 represents the filing level. FIG. 17 illustrates the same venous air capture chamber as FIGS. 16a-d, but with a 65% filling level as represented by line 1701.

The legend for FIGS. 16a-d transitions from a high velocity flow in red at 1.04e-01 m/s, orange at 8.58e-02 m/s, yellow at 7.02e-02 m/s, green at 4.96e-02 m/s to light blue at 2.87e-02 m/s to a low velocity flow shown in blue at 1.07e-05 m/s. The legend for FIG. 17 transitions from a high velocity flow in red at 1.04e-01 m/s, orange at 8.58e-02 m/s, yellow at 7.02e-02 m/s, green at 4.96e-02 m/s to light blue at 2.87e-02 m/s to a low velocity flow shown in blue at 4.15e-06 m/s.

In setting a filling level for a particular inlet flow velocity, flow without turbulence at the fluid-air interface is important to minimize residence time of blood in the area and to avoid trapping air bubbles in the fluid. As shown in each of FIGS. 16a-d, there is a transit area between the massive flow having a high velocity in green area 1603 and the fluid-air interface, shown as blue area 1602 in FIGS. 16a-d. A lower velocity blue area 1604 also exists at the bottom of the air capture chamber. In FIG. 17, a blue transit area 1702 exists between the massive flow in green area 1703 and the fluid air interface 1701. A lower velocity blue area 1704 also exists near the bottom of the air capture chamber. In the transit area, the velocity is low relative to the massive flow. However, in comparing FIGS. 16a-d to 17, the transit area is smaller in FIGS. 16a-d. The results suggest that the filling level of the venous air capture chamber can be used to minimize the transit area, and that for an inlet flow velocity of 0.104 m/s, a filling level of no more than 60% should be used. In each of the figures illustrated in FIGS. 18-25, the conditions used are a fluid inlet flow velocity of 0.104 m/s or 100 mL/min and a 60% filling level.

Figure 18A:
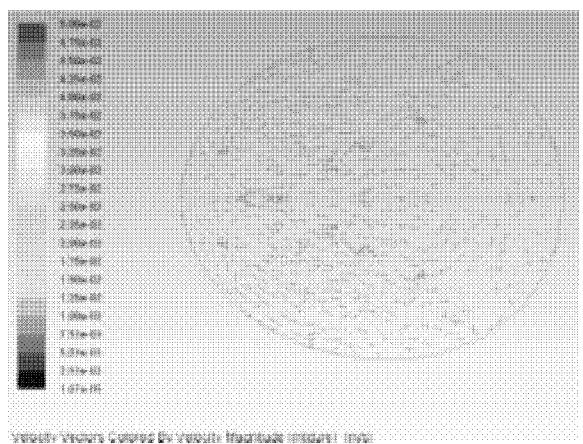
FIGS. 18a-d show y-section views the velocity distribution vectors with a 60% filling level and an inlet velocity of 0.104 m/s.
Figure 18B:
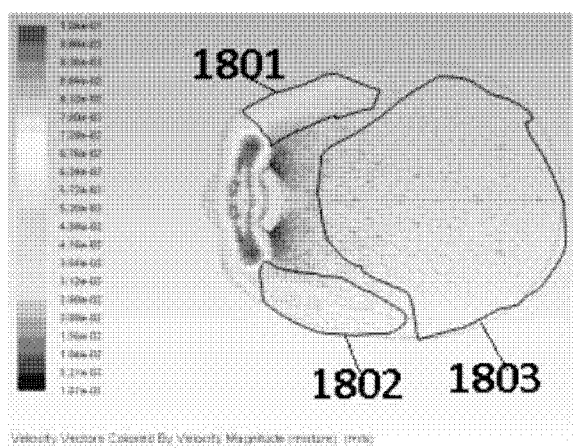
Figure 18C:
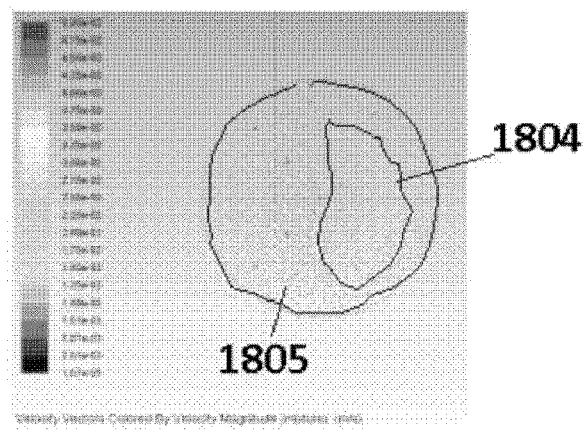
Figure 18D:
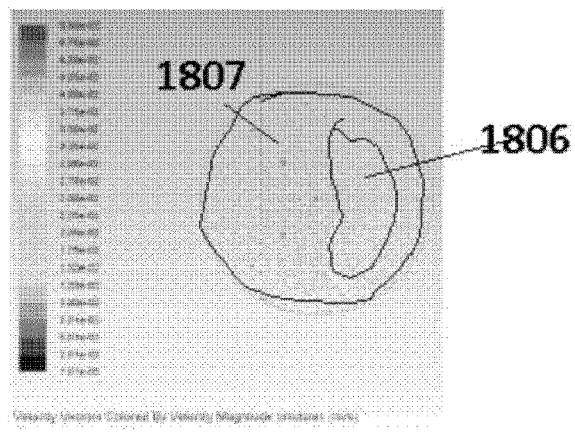

FIGS. 18a-18d illustrate cross sections of the velocity distribution vectors at various heights in the chamber body. FIG. 18a shows the cross section at a height of 7.5 cm, set as the fluid-air interface in the conditions of a 60% filling level in a 12.5 cm venous air capture chamber. FIG. 18b shows the cross section at a height of 6 cm, FIG. 18c shows the cross section at a height of 4 cm, and FIG. 18d shows the cross section at a height of 3 cm. The legend for FIGS. 18a, c, and d transitions from a high velocity flow in red at 5.00e-02 m/s, orange at 4.13e-02 m/s, yellow at 3.38e-02 m/s, green at 2.13e-02 m/s to light blue at 1.13e-02 m/s to a low velocity flow shown in blue at 1.07e-05 m/s. The legend for FIG. 18b transitions from a high velocity flow in red at 1.04e-01 m/s, orange at 8.58e-02 m/s, yellow at 7.02e-02 m/s, green at 4.96e-02 m/s to light blue at 2.87e-02 m/s to a low velocity flow shown in blue at 1.07e-05 m/s.

As shown in FIG. 18a, the velocity is maintained at the fluid-air interface, though the velocity is low, as all velocity vectors are in blue. The fluid near the fluid inlet port, shown in FIG. 18b, is uniform, with higher velocities in green areas 1801 and 1802, and lower velocity in blue area 1803. FIG. 18c illustrates light blue portion 1804, and blue portion 1805. FIG. 18d illustrates light blue portion 1806, and blue portion 1807. There are no observable areas of stagnant flow at any level. However, as shown in FIG. 18b, the fluid exhibits a circular flow, which may create a longer residence time.

Figure 19A:
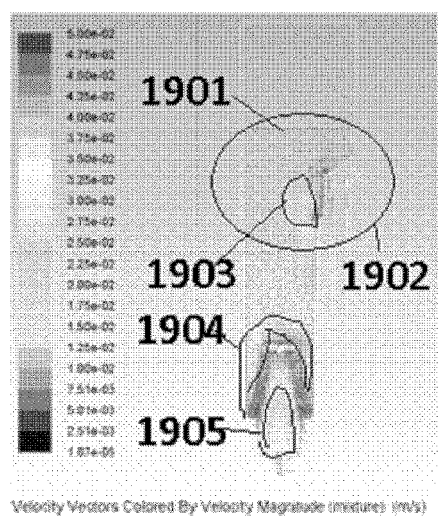
FIGS. 19a-b show z-section views the velocity distribution vectors with a 60% filling level and an inlet velocity of 0.104 m/s.
Figure 19B:
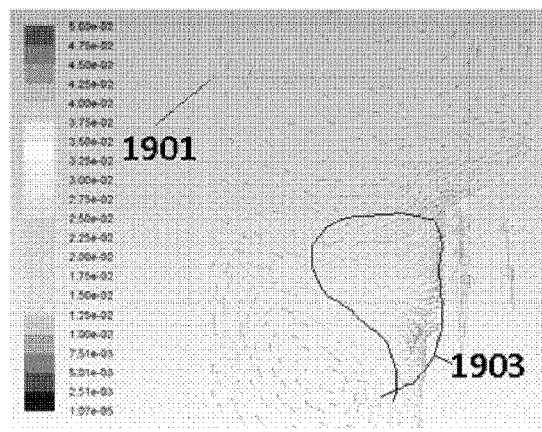

FIGS. 19a and 19b show section views of the velocity distribution vectors in the plane at z=0, or the symmetry plane. FIG. 19b is a close up view of the area in circle 1902 of FIG. 19a. In each of FIGS. 19a and 19b, line 1901 represents the filling level, set at 60%. The legend for FIGS. 19a-b transitions from a high velocity flow in red at 5.00e-02 m/s, orange at 3.83e-02 m/s, yellow at 3.38e-02 m/s, green at 2.13e-02 m/s to light blue at 1.13e-02 m/s to a low velocity flow shown in blue at 1.07e-05 m/s.

FIGS. 19a-b illustrate light blue areas 1903 and 1904, as well as green area 1905. The remainder of the fluid is shown in blue. As shown in FIGS. 19a and 19b, there are no observable areas of stagnant flow. However, as shown in FIG. 19b, a circular flow is present, which may increase residence time.

Figure 20A:
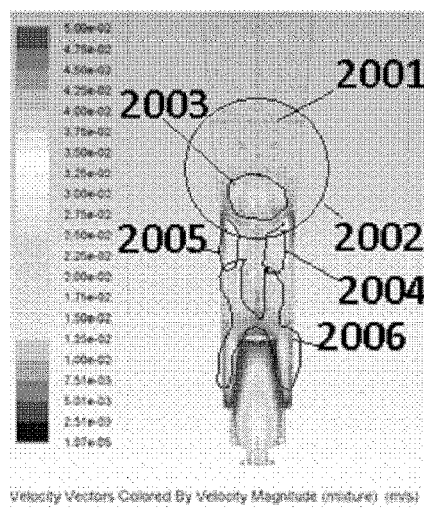
FIGS. 20a-b show x-section views the velocity distribution vectors with a 60% filling level and an inlet velocity of 0.104 m/s.
Figure 20B:
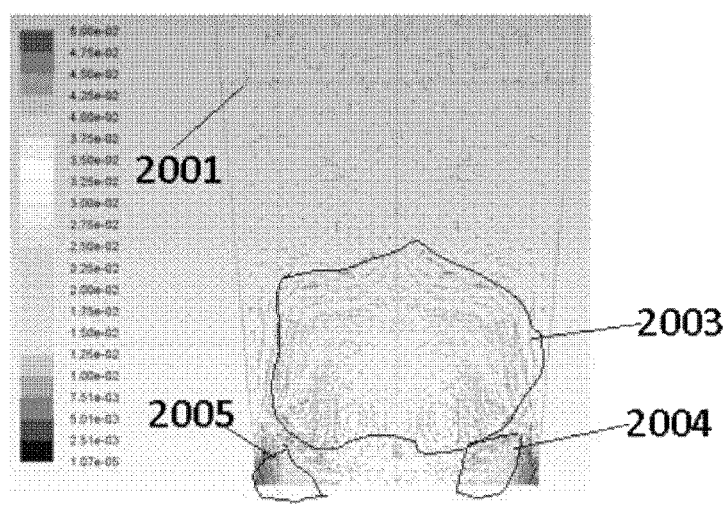

FIGS. 20a and 20b show section views of the velocity distribution chambers at a section of x=0, which is across a center line of the small diameter cylinder portion. In each of FIGS. 20a and 20b, the line marked 2001 represents the filling level of 60%. FIG. 20b is a close up view of the area in FIG. 20a shown in circle 2002. The legend for FIGS. 20a-b transitions from a high velocity flow in red at 5.00e-02 m/s, orange at 3.83e-02 m/s, yellow at 3.38e-02 m/s, green at 2.13e-02 m/s to light blue at 1.13e-02 m/s to a low velocity flow shown in blue at 1.07e-05 m/s. In FIGS. 20a-b, areas 2003 and 2006 are in light blue, while areas 2004 and 2005 are in green.

As shown, there are no areas of stagnant flow within the venous air capture chamber. However, an area of circle flow exists, which may increase residence time. As illustrated in FIGS. 16-20, areas of circular flow exist within the venous air capture chamber at the conditions of an inlet flow rate of 100 mL/min and a 60% filling level. Fluid within the circular flow areas will stay in the chamber for a longer time, causing a risk for a treatment with low inlet flow rate, such as 100 ml/min and below. The circular flow areas are largely reduced when flow rate increases, as described herein.

Figure 21A:
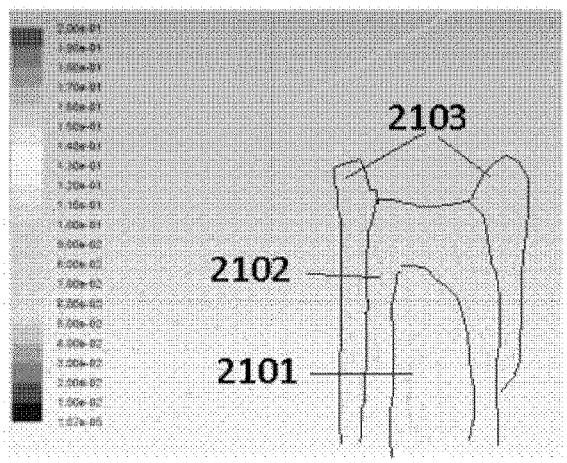
FIGS. 21a-b show velocity distribution vectors near the inlet ports with a 60% filling level and an inlet velocity of 0.104 m/s.
Figure 21B:
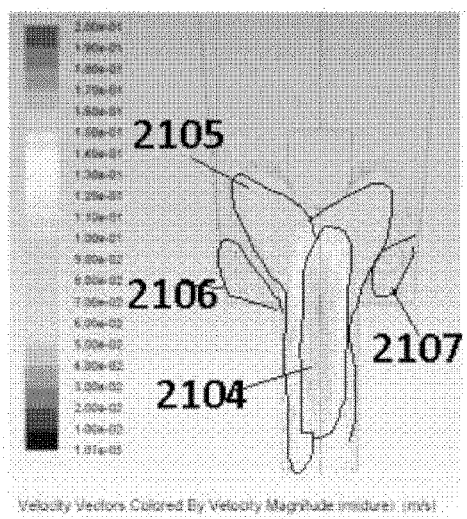

FIGS. 21a and 21b illustrate velocity distribution within the inlet ports. The legend for FIGS. 21a-b transitions from a high velocity flow in red at 2.00e-01 m/s, orange at 1.65e-01 m/s, yellow at 1.35e-01 m/s, green at 8.50e-02 m/s to light blue at 5.50e-02 m/s to a low velocity flow shown in blue at 1.07e-05 m/s. FIG. 21a shows red area 2101, green area 2102, and blue areas 2103. FIG. 21b shows red area 2104, green area 2105 and blue areas 2106 and 2107. As shown in FIGS. 21a and 21b, there are no low velocity or stagnant flow areas within the inlet ports.

Figure 22A:
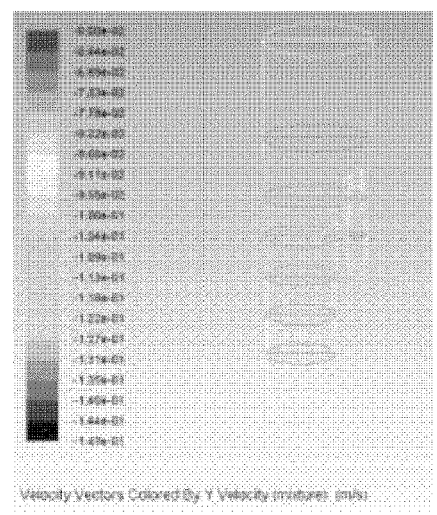
FIGS. 22a-b show shows velocity distribution vectors in the y-direction with a 60% filling level and an inlet velocity of 0.104 m/s.
Figure 22B:
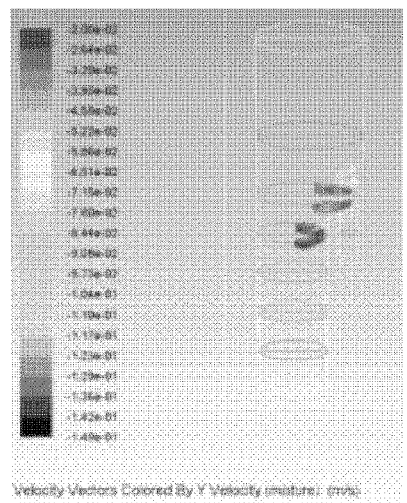

FIGS. 22a and 22b show section views of the velocity in the y-direction through the chamber body through multiple sectional planes. In FIG. 22a, the max velocity scale is set at 0.06 m/s, meaning only velocities in excess of 0.06 m/s are shown. In FIG. 22b, the max velocity scale is set at 0.02 m/s, meaning velocities of greater than 0.02 m/s are shown. The legend for FIG. 22a transitions from a low velocity flow in red at −6.00 e-02 m/s, orange at −7.11e-02 m/s, yellow at −8.86e-01 m/s, green at −1.07e-01 m/s to light blue at −1.25e-01 m/s to a high velocity flow shown in blue at −1.49e-01 m/s. The legend for FIG. 22b transitions from a low velocity flow in red at −2.00 e-02 m/s, orange at −4.26e-02 m/s, yellow at −6.16e-02 m/s, green at −9.41e-02 m/s to light blue at −1.14e-01 m/s to a high velocity flow shown in blue at −1.49e-01 m/s. All visible velocity vectors are shown in red. As described, an important function of the venous air capture chamber is to capture air bubbles in the blood before the blood is passed back to the patient. In order to capture bubbles, fluid velocity in y direction should be maintained at less than 0.06 m/s (ref to Replacement of Renal Function by Dialysis, $5^{th}$ edition). As shown in FIG. 22a, no velocity vectors of greater than 0.06 m/s are shown which means that velocity in the y-direction is less than 0.06 m/s. As shown in FIG. 22b, velocities of 0.02 m/s or greater do exist within the chamber.

Figure 23:
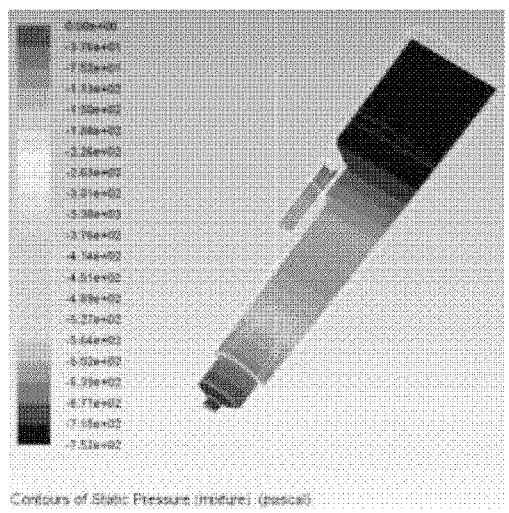
FIG. 23 shows the pressure distribution in the venous air capture chamber with a 60% filling level and an inlet velocity of 0.104 m/s.

FIG. 23 is a representative pressure distribution within the venous air capture chamber, which shows the pressure distribution. At the conditions of a 100 ml/min flow rate, the pressure ranges from −752 to 0 Pa or −5.6 mmHg to 0 mmHg. The legend in FIG. 23 transitions from red at 0.00 pascal, to orange at −1.69e+02 pascal, yellow at −2.42e+02 pascal, green at −4.32e+2 pascal, to light blue at −5.82e+02 pascal, to a low in blue of −7.52e+02 pascal. The pressure is greatest near the outlet of the venous air capture chamber, and decreases with increasing height through the venous air capture chamber.

Figure 24A:
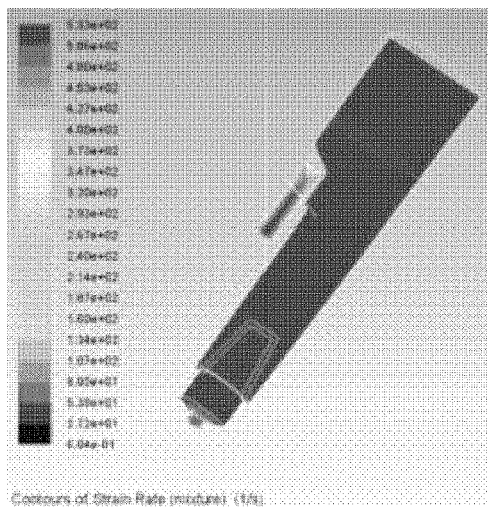
FIGS. 24a-c show the max shear rate with a 60% filling level and an inlet velocity of 0.104 m/s.
Figure 24B:
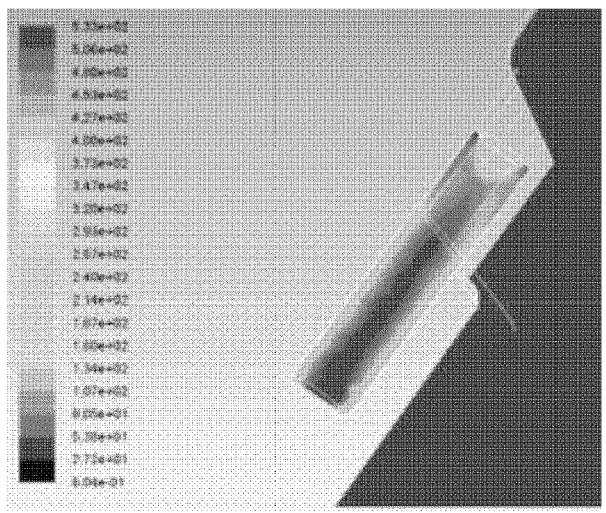
Figure 24C:
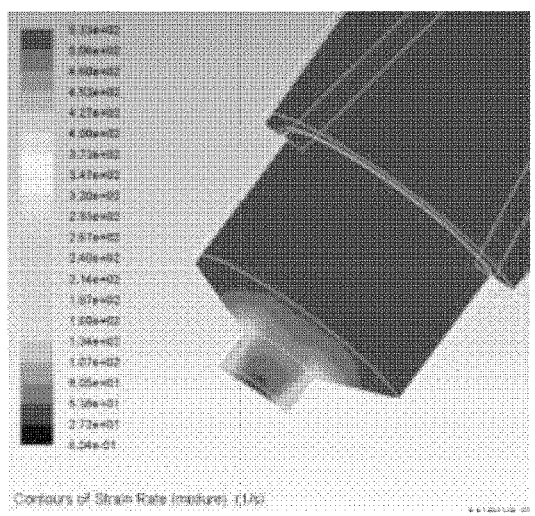

Improper flow conditions through the venous air capture chambers, such as high shear stress, may result in a dangerous level of hemolysis, which can be dangerous to the patient. As recommended (ref Kidney Int, Paul et al, 2003), the shear stress thresholds for red blood cell damage are 4000 dynes/cm$^2$ (400 Pa) for short term exposure and 2000 dynes/cm$^2$ (200 Pa) long term exposure. FIG. 24a shows a representative strain distribution within the chamber body at a plane of z=0, which is a proper representation to show strain distribution. FIGS. 24b and 24c are the representative strain distributions near the fluid inlet and fluid outlet, respectively. The legend for FIG. 24a-c transitions from a shear stress in red at 5.33 e+02 1/s, orange at 4.40e+02 1/s, yellow at 3.60e+02 1/s, green at 2.54e+02 1/s to light blue at 1.21e+02 1/s to a low shear stress shown in blue at 6.04e-01 1/s. All visible shear stress is shown in green. As shown in FIG. 24a, the maximum shear rate is about 533 1/s or a max shear stress (considering a viscosity of 0.00271 PaS) of 1.45 Pa, which is much less than the safety thresholds. As such, the venous air capture chambers described can be safely used for a patient with an inlet flow velocity of 100 ml/min and a filling level of 60%. As shown in FIG. 24a, the highest levels of strain are concentrated at the fluid inlet and outlet. However, as shown in FIGS. 24b and 24c, the highest strain levels still remain well below the dangerous levels.

Figure 25:
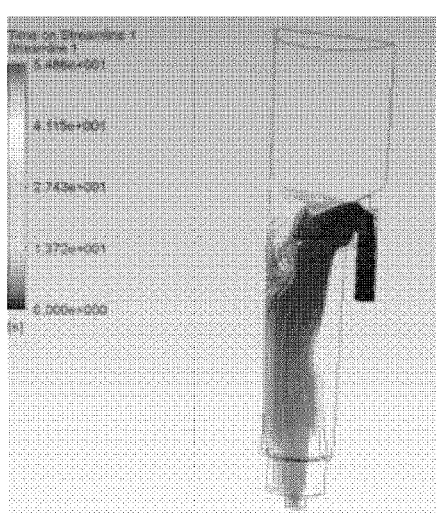
FIG. 25 shows residence time distributions with a 60% filling level and an inlet velocity of 0.104 m/s.

FIG. 25 shows a residence time distribution within the venous air capture chamber with the conditions of 100 ml/min inlet flow rate and a 60% filling level. As shown in FIG. 25, the maximum residence time is about 54 seconds. Due to limits of ANSYS Fluent, only a 3D residence time distribution is presented.

Experiment 7

Figure 26A:
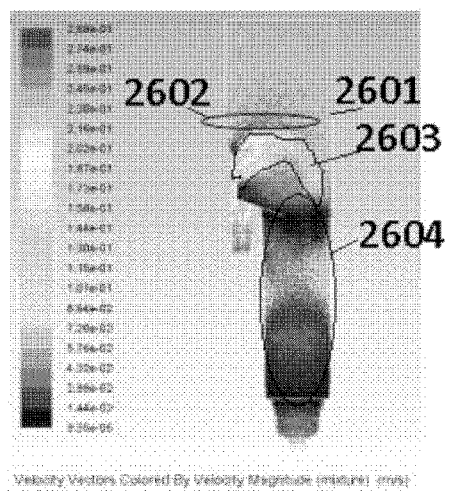
FIGS. 26a-d show velocity distribution vectors with a 65% filling level and an inlet velocity of 0.288 m/s.
Figure 26B:
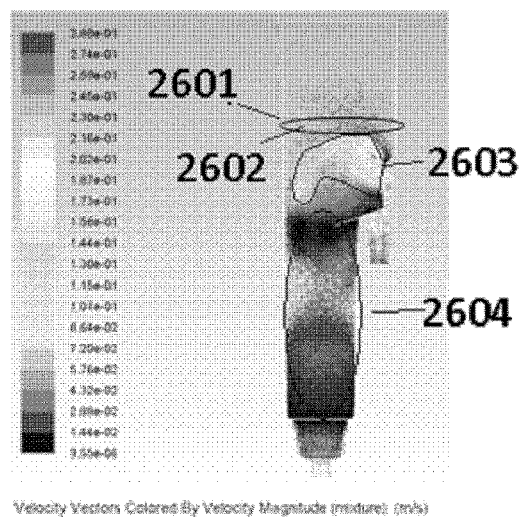
Figure 26C:
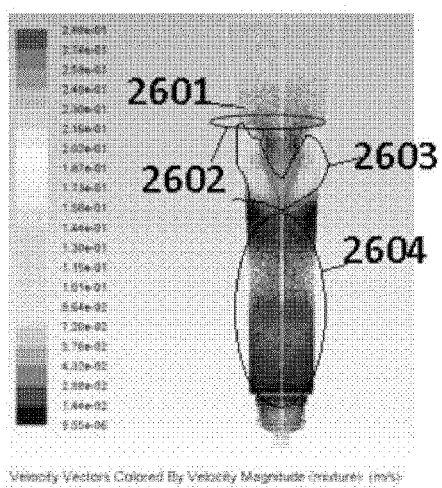
Figure 26D:
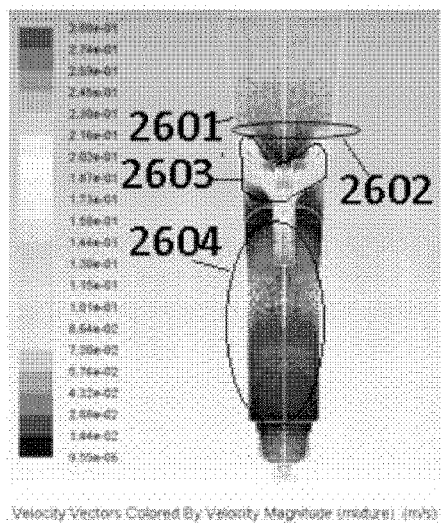
Figure 27:
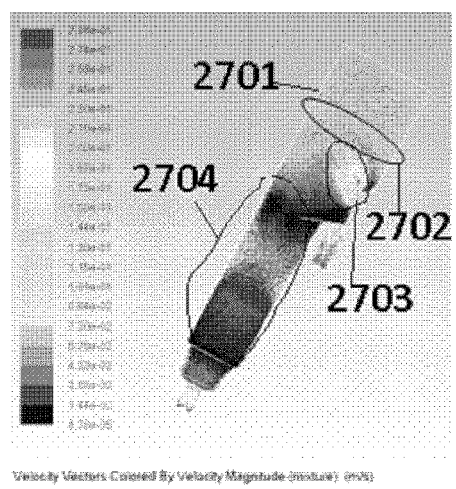
FIG. 27 shows a velocity distribution vector with a 75% filling level and an inlet velocity of 0.288 m/s.

FIGS. 26a-d illustrate velocity distribution vectors for such a venous air capture chamber at the conditions of a 65% filling level and 0.288 m/s inlet velocity, corresponding to a flow rate of 275 mL/min, for a venous air capture chamber as described comprising a mesh filter on the fluid outlet. FIG. 26a illustrates a front view of the chamber body, FIG. 26b illustrates a back view of the chamber body, FIG. 26c illustrates a right side view of the chamber body, and FIG. 26d illustrates a left-side view of the chamber body. In each of FIGS. 26a-d, the line 2601 represents the filing level. FIG. 27 illustrates the same venous air capture chamber as FIGS. 26a-d, but with a 75% filling level as represented by line 2701. The legend for FIGS. 26a-d and 27 transitions from a high velocity flow in red at 2.88 e-01 m/s, orange at 2.37e-01 m/s, yellow at 1.95e-01 m/s, green at 1.38e-01 m/s to light blue at 7.92-02 m/s to a low velocity flow shown in blue at 9.55 e-06 m/s.

As shown in each of FIGS. 26a-d, there is a transit area between the massive flow green area 2603 having a high velocity and the fluid-air interface 2601, shown as area 2602 in FIGS. 26a-d. A lower velocity blue area 2604 exists near the bottom of the air capture chamber. In FIG. 27, there is a transit area 2702 between green massive flow area 2703 and the fluid air interface 2701. A lower velocity blue area 2704 exists near the bottom of the air capture chamber. In the transit area, the velocity is low relative to the massive flow. However, in comparing FIGS. 26a-d to 27, the transit area is smaller in FIGS. 26a-d. The results suggest that the filling level of the venous air capture chamber can be used to minimize the transit area, and that for an inlet flow velocity of 0.288 m/s, a filling level of no more than 65% should be used. In each of the figures illustrated in FIGS. 28-35, the conditions used are a fluid inlet flow velocity of 0.288 m/s or 275 mL/min and a 65% filling level.

Figure 28A:
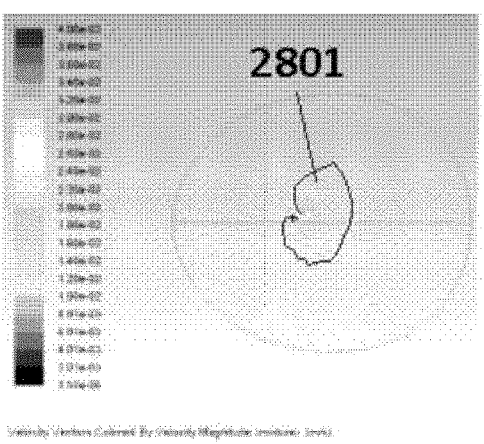
FIG. 28a-d show y-section views the velocity distribution vectors with a 65% filling level and an inlet velocity of 0.288 m/s.
Figure 28B:
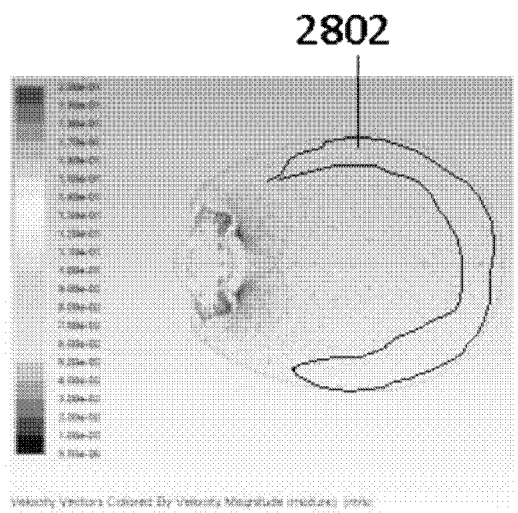
Figure 28C:
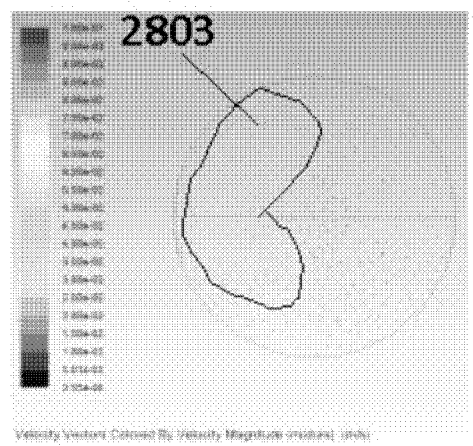
Figure 28D:
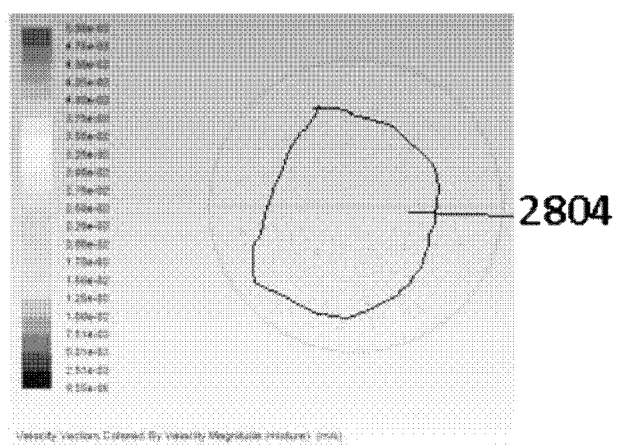

FIGS. 28a-28d illustrate cross sections of the velocity distribution vectors at various heights in the chamber body. FIG. 28a shows the cross section at a height of 7.75 cm, set as the fluid-air interface in the conditions of a 65% filling level in a 12.5 cm venous air capture chamber. FIG. 28b shows the cross section at a height of 6 cm, FIG. 28c shows the cross section at a height of 4 cm, and FIG. 28d shows the cross section at a height of 3 cm. The legend for FIG. 28a transitions from a high velocity flow in red at 4.00 e-02 m/s, orange at 3.30e-02 m/s, yellow at 2.70e-02 m/s, green at 1.90e-02 m/s to light blue at 1.10e-02 m/s to a low velocity flow shown in blue at 9.55 e-06 m/s. The legend for FIG. 28b transitions from a high velocity flow in red at 2.00 e-01 m/s, orange at 1.65e-01 m/s, yellow at 1.35e-01 m/s, green at 8.50e-02 m/s to light blue at 5.50e-02 m/s to a low velocity flow shown in blue at 9.55e-06 m/s. The legend for FIG. 28c transitions from a high velocity flow in red at 1.00 e-01 m/s, orange at 8.25e-02 m/s, yellow at 6.75e-02 m/s, green at 4.75e-02 m/s to light blue at 2.25e-02 m/s to a low velocity flow shown in blue at 9.55e-06 m/s. The legend for FIG. 28a transitions from a high velocity flow in red at 5.00 e-02 m/s, orange at 3.83e-02 m/s, yellow at 3.38e-02 m/s, green at 2.13e-02 m/s to light blue at 1.38e-02 m/s to a low velocity flow shown in blue at 9.55e-06 m/s.

FIG. 28a shows light blue area 2801, while the rest of the diagram is blue. FIG. 28b shows light blue area 2802, while the rest of the diagram is blue. FIG. 28c shows light blue area 2803 while the rest of the diagram is blue. FIG. 28d shows green area 2804 while the rest of the diagram is blue. As shown in FIG. 28a, the velocity is maintained at the fluid-air interface, though the velocity is low. There are no observable areas of stagnant flow at any level. Distribution of velocity became uniform on the planes from Y=4 cm to Y=3 cm gradually as shown in FIGS. 28c and 28d. As shown in FIG. 28b, there is some circular flow, but the areas of circular flow are largely reduced as compared to the lower flow rates depicted in Experiment 6.

Figure 29A:
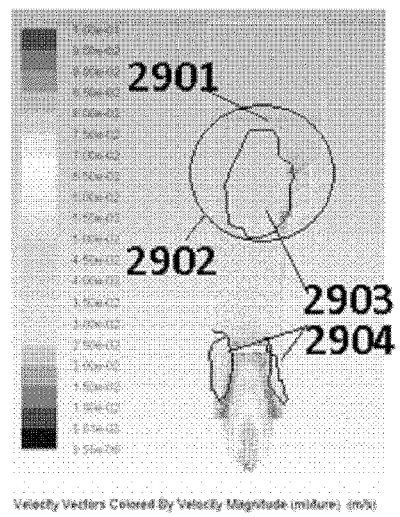
FIGS. 29a-b show z-section views the velocity distribution vectors with a 65% filling level and an inlet velocity of 0.288 m/s.
Figure 29B:
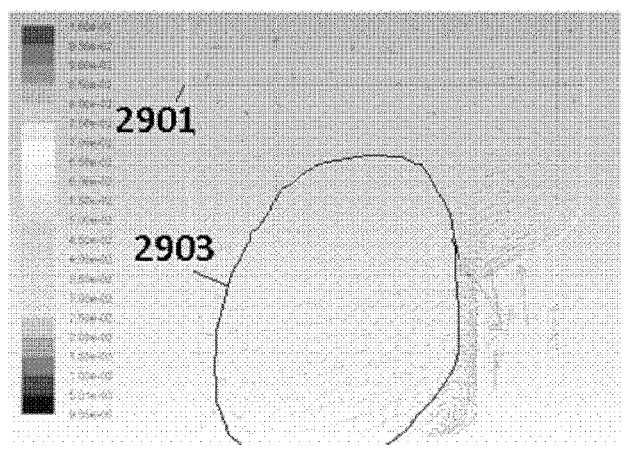

FIGS. 29a and 29b show section views of the velocity distribution vectors in the plane at z=0, or the symmetry plane. FIG. 29b is a close up view of the area in circle 2902 of FIG. 29a. In each of FIGS. 29a and 29b, line 2901 represents the filling level, set at 65%. The legend for FIGS. 29a-b transitions from a high velocity flow in red at 1.00 e-01 m/s, orange at 8.25e-02 m/s, yellow at 6.75e-02 m/s, green at 4.25e-02 m/s to light blue at 2.25e-02 m/s to a low velocity flow shown in blue at 9.55e-06 m/s. Area 2903 is green, area 2904 is light blue, and the remainder of the air capture chamber is in blue. As shown in FIGS. 29a and 29b, there are no observable areas of stagnant flow. Additionally, as noted, areas of circular flow are largely reduced. Velocity in the small diameter cylinder portion of the venous air capture chamber is uniform under the conditions.

Figure 30A:
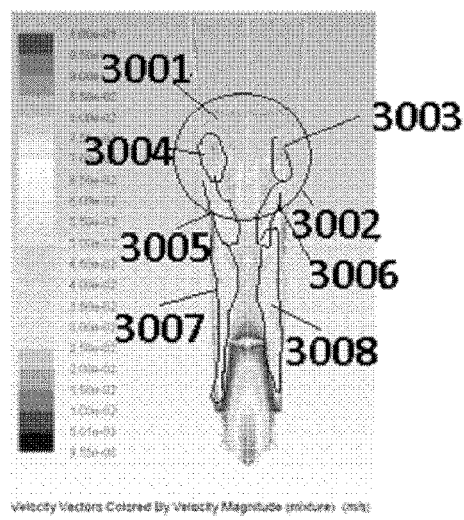
FIGS. 30a-b show x-section views the velocity distribution vectors with a 65% filling level and an inlet velocity of 0.288 m/s.
Figure 30B:
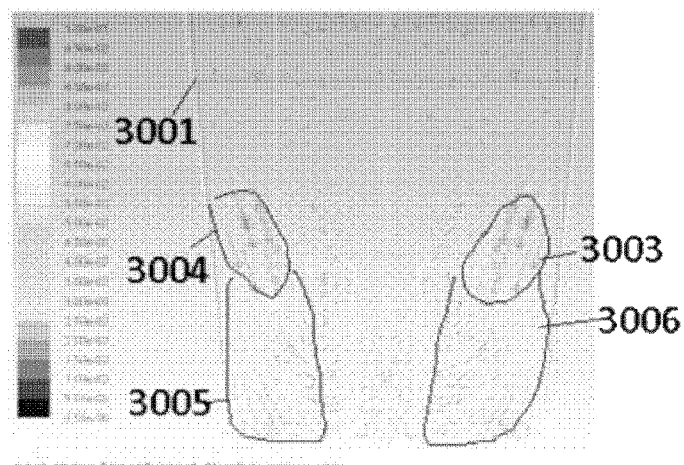

FIGS. 30a and 30b show section views of the velocity distribution chambers at a section of x=0, which is across a center line of the small diameter cylinder portion. In each of FIGS. 30a and 30b, the line marked 3001 represents the filling level of 65%. FIG. 30b is a close up view of the area in FIG. 30a shown in circle 3002. The legend for FIGS. 30a-b transitions from a high velocity flow in red at 1.00 e-01 m/s, orange at 8.25e-02 m/s, yellow at 6.75e-02 m/s, green at 4.25e-02 m/s to light blue at 2.25e-02 m/s to a low velocity flow shown in blue at 9.55e-06 m/s. Areas 3003 and 3004 are red, areas 3005 and 3006 are green, areas 3007 and 3008 are light blue, and the remainder of the air capture chamber is in blue. As shown, there are no areas of stagnant flow within the venous air capture chamber. Further, areas of circular flow are largely reduced as compared to the diagrams presented in Experiment 6.

Figure 31A:
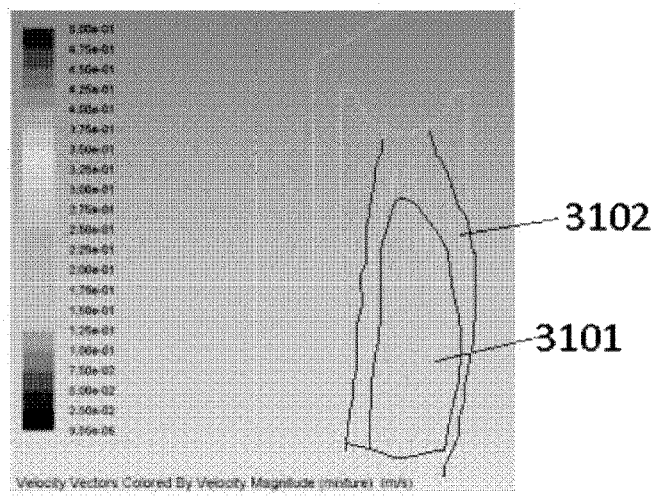
FIGS. 31a-b show velocity distribution vectors near the inlet ports with a 65% filling level and an inlet velocity of 0.288 m/s.
Figure 31B:
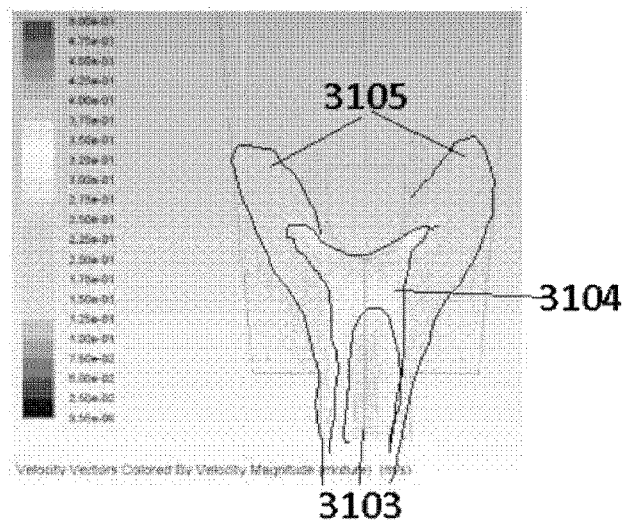

FIGS. 31a and 31b illustrate velocity distribution within the inlet ports. The legend for FIGS. 3a-b transitions from a high velocity flow in red at 5.00 e-01 m/s, orange at 3.83e-01 m/s, yellow at 3.38e-01 m/s, green at 2.38e-01 m/s to light blue at 1.38e-01 m/s to a low velocity flow shown in blue at 9.55e-06 m/s. In FIG. 31a, area 3101 is red, area 3102 is green, and the remainder is blue. In FIG. 31b, area 3103 is red, area 3104 is yellow, area 3105 is green, and the remainder is blue. As shown in FIGS. 31a and 31b, no low velocity or stagnant flow areas are present within the inlet ports.

Figure 32A:
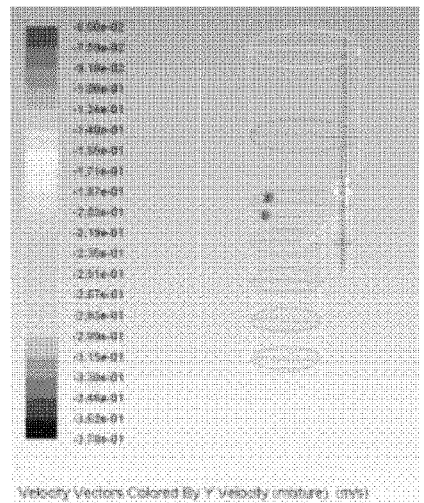
FIGS. 32a-b show velocity distribution vectors in the y-direction with a 65% filling level and an inlet velocity of 0.288 m/s.
Figure 32B:
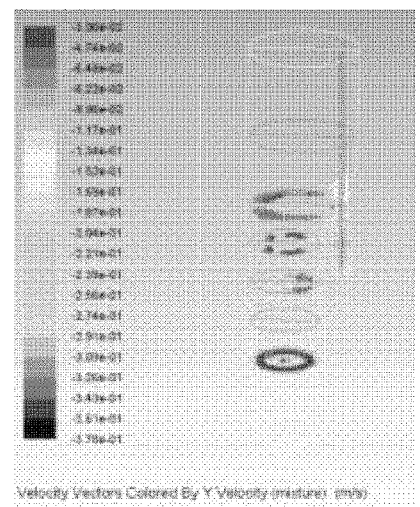

FIGS. 32a and 32b show section views of the velocity in the y-direction through the chamber body through multiple sectional planes. In FIG. 32a, the max velocity scale is set at 0.06 m/s, meaning only velocities in excess of 0.06 m/s are shown. In FIG. 32b, the max velocity scale is set at 0.03 m/s, meaning velocities of greater than 0.03 m/s are shown. The legend for FIG. 32a transitions from a low velocity flow in red at −6.00 e-02 m/s, orange at −1.16e-01 m/s, yellow at −1.63e-01 m/s, green at −2.27e-01 m/s to light blue at −2.91e-01 m/s to a high velocity flow shown in blue at −3.78e-01 m/s. The legend for FIG. 32b transitions from a low velocity flow in red at −3.00 e-02 m/s, orange at −1.06e-01 m/s, yellow at −1.43e-01 m/s, green at −2.30e-01 m/s to light blue at −1.14e-01 m/s to a high velocity flow shown in blue at −3.78e-01 m/s. All visible velocity vectors are shown in red.

As shown in FIG. 32a, only a very few velocity vectors of greater than 0.06 m/s are shown which means that velocity in the y-direction is less than 0.06 m/s with a few exceptions. As shown in FIG. 32b, velocities of 0.03 m/s or greater do exist within the chamber.

Figure 33:
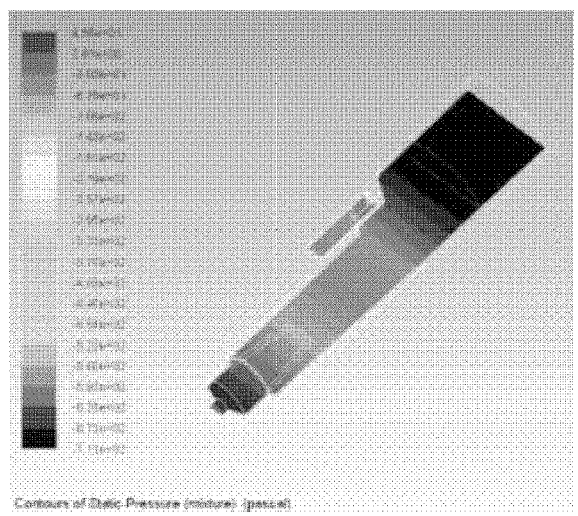
FIG. 33 shows the pressure distribution in the venous air capture chamber with a 65% filling level and an inlet velocity of 0.288 m/s.

FIG. 33 is a representative pressure distribution within the venous air capture chamber, which shows the pressure distribution. The legend in FIG. 33 transitions from red at 4.56e+01 pascal, to orange at −8.69e+01 pascal, yellow at −2.00e+02 pascal, green at −3.89e+02 pascal, to light blue at −5.03e+02 pascal, to a low in blue of −7.11e+02 pascal. The pressure is greatest near the outlet of the venous air capture chamber, and decreases with increasing height through the venous air capture chamber. At the conditions of a 275 ml/min flow rate, the pressure ranges from −711 to 45.6 Pa or −5.3 mmHg to 0.34 mmHg. The pressure is greatest near the outlet of the venous air capture chamber, and decreases with increasing height through the venous air capture chamber.

Figure 34A:
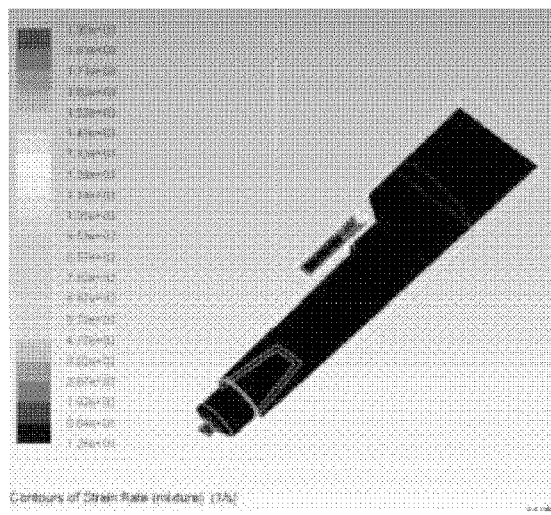
FIGS. 34*a-c* show the max shear rate with a 65% filling level and an inlet velocity of 0.288 m/s.
Figure 34B:
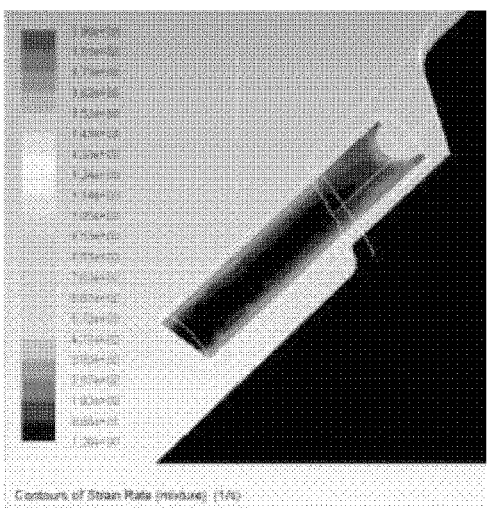
Figure 34C:
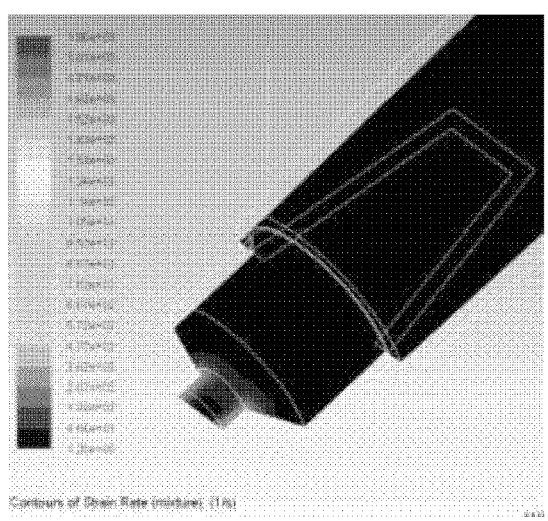

FIG. 34a shows a representative strain distribution within the chamber body at a plane of z=0, which is a proper representation to show strain distribution. The legend for FIG. 34a-c transitions from a shear stress in red at 1.90e+03 1/s, orange at 1.62e+03 1/s, yellow at 1.24e+03 1/s, green at 9.53e+02 1/s to light blue at 2.87e+02 1/s to a low shear stress shown in blue at 1.26e-0 1/s. All visible shear stress is shown in green. As shown in FIG. 34a, the maximum shear rate is about 1900 1/s or a max shear stress (considering a viscosity of 0.00271 PaS) of 5.1 Pa, which is much less than the safety thresholds. As such, the venous air capture chambers described can be safely used for a patient with an inlet flow velocity of 275 ml/min and a filling level of 65%. FIGS. 34b and 34c are the representative strain distributions near the fluid inlet and fluid outlet, respectively. As shown in FIG. 34a, the highest levels of strain are concentrated at the fluid inlet and outlet. However, as shown in FIGS. 34b and 34c, the strain levels still remain well below the dangerous levels.

Figure 35:
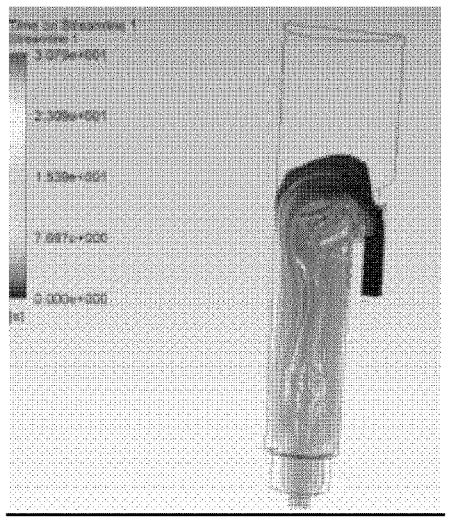
FIG. 35 shows residence time distributions with a 65% filling level and an inlet velocity of 0.288 m/s.

FIG. 35 shows a residence time distribution within the venous air capture chamber with the conditions of 275 ml/min inlet flow rate and a 65% filling level. As shown in FIG. 35, the maximum residence time is about 31 seconds. Due to limits of ANSYS Fluent, only a 3D residence time distribution is presented.

Experiment 8

Figure 36A:
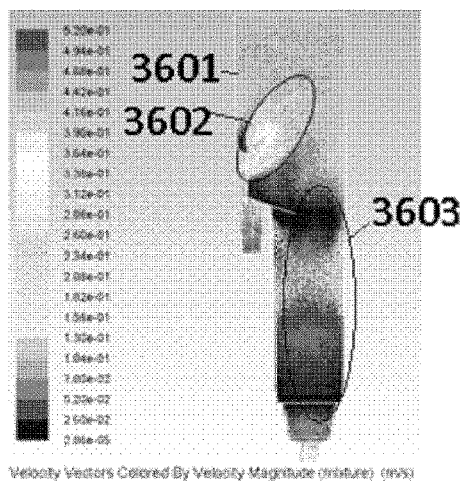
FIGS. 36*a-d* show velocity distribution vectors with a 75% filling level and an inlet velocity of 0.52 m/s.
Figure 36B:
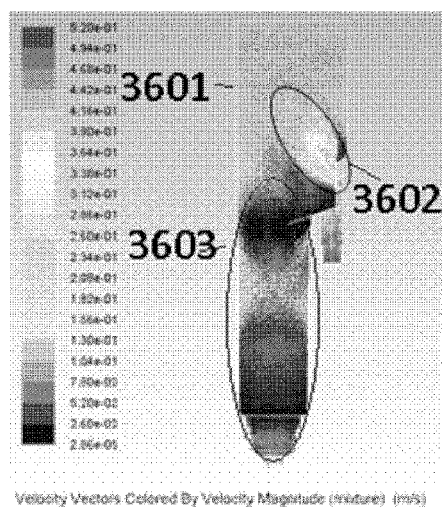
Figure 36C:
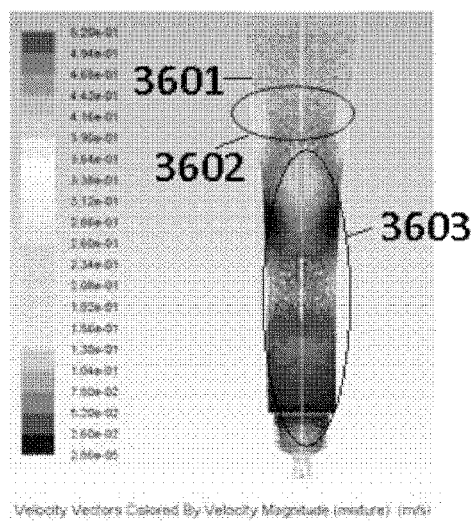
Figure 36D:
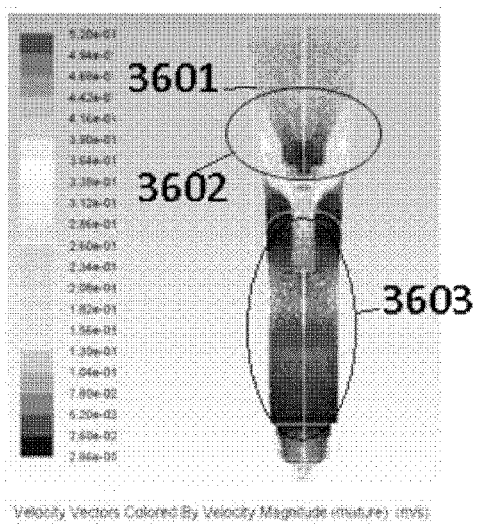

FIGS. 36a-d illustrate velocity distribution vectors for such a venous air capture chamber at the conditions of a 75% filling level and 0.52 m/s inlet velocity, corresponding to a flow rate of 500 mL/min, for a venous air capture chamber as described comprising a mesh filter on the fluid outlet. FIG. 36a illustrates a front view of the chamber body, FIG. 36b illustrates a back view of the chamber body, FIG. 36c illustrates a right side view of the chamber body, and FIG. 36d illustrates a left-side view of the chamber body. In each of FIGS. 36a-d, the line 3601 represents the filing level. The legend for FIGS. 36a-d transitions from a high velocity flow in red at 5.20 e-01 m/s, orange at 4.27e-01 m/s, yellow at 3.51e-01 m/s, green at 2.22e-01 m/s to light blue at 1.44e-01 m/s to a low velocity flow shown in blue at 2.86e-05 m/s.

As shown in each of FIGS. 36a-d, there is almost no transit area between the massive flow green area 3602 having a high velocity and the fluid-air interface with the conditions of a 500 mL/min flow rate and a 75% filling level. A lower velocity blue area 3603 exists near the bottom of the air capture chamber. The results suggest that the filling level of the venous air capture chamber of no more than 75% should be used when the fluid inlet velocity is 500 mL/min. In each of the figures illustrated in FIGS. 36-44, the conditions used are a fluid inlet flow velocity of 0.52 m/s or 500 mL/min and a 75% filling level.

Figure 37A:
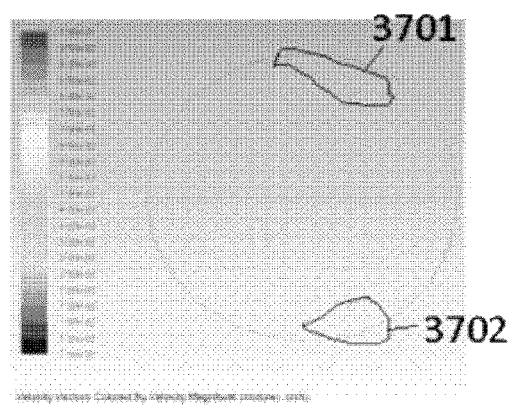
FIGS. 37*a-d* show y-section views the velocity distribution vectors with a 75% filling level and an inlet velocity of 0.52 m/s.
Figure 37B:
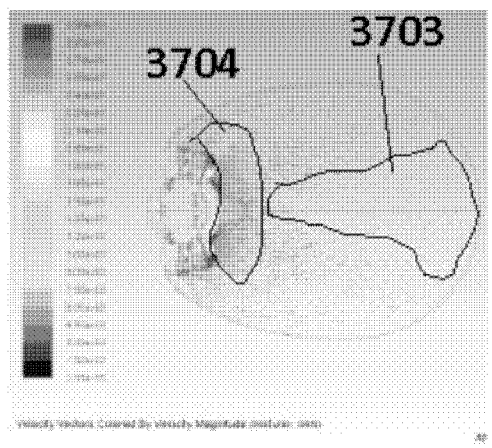
Figure 37C:
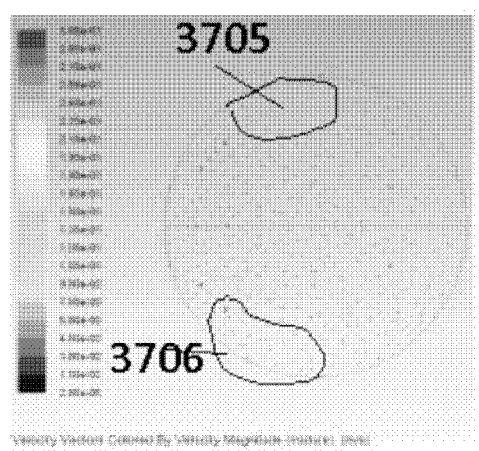
Figure 37D:
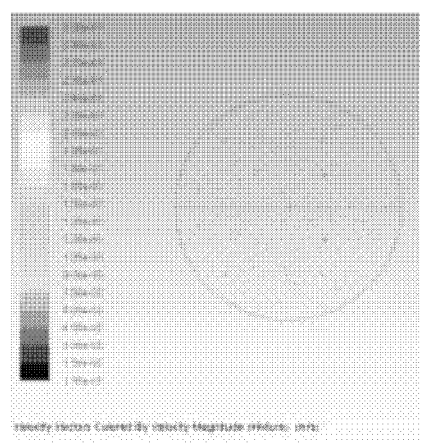

FIGS. 37a-37d illustrate cross sections of the velocity distribution vectors at various heights in the chamber body. FIG. 37a shows the cross section at a height of 8.5 cm, set as the fluid-air interface area in the conditions of a 75% filling level in a 12 cm venous air capture chamber. FIG. 37b shows the cross section at a height of 6 cm, FIG. 37c shows the cross section at a height of 4 cm, and FIG. 387 shows the cross section at a height of 3 cm. The legend for FIG. 37a transitions from a high velocity flow in red at 1.00 e-01 m/s, orange at 8.25e-02 m/s, yellow at 6.75 e-02 m/s, green at 4.25e-02 m/s to light blue at 2.75e-02 m/s to a low velocity flow shown in blue at 2.86e-05 m/s. The legend for FIGS. 37b-d transitions from a high velocity flow in red at 3.00 e-01 m/s, orange at 2.38e-01 m/s, yellow at 2.03e-01 m/s, green at 1.42e-01 m/s to light blue at 6.75e-02 m/s to a low velocity flow shown in blue at 2.86e-05 m/s. FIG. 37a includes green areas 3701 and 3702, while the remainder of the diagram is blue. FIG. 37b includes green area 3703, light blue area 3704, and the remainder of the diagram is blue. FIG. 37c includes light blue areas 3705 and 3706 while the remainder of the diagram is blue. FIG. 37d includes only blue velocity vectors.

As shown in FIG. 37a, the velocity is maintained at the fluid-air interface area. There are no observable areas of stagnant flow at any level. Distribution of velocity became uniform on the planes from Y=4 cm gradually as shown in FIG. 37c and more uniform on the plane at Y=3 cm, as shown in FIG. 37d. As shown in FIG. 37b, there is some circular flow, but the areas of circular flow are largely reduce as compared to the lower flow rates depicted in Experiments 6 and 7.

Figure 38A:
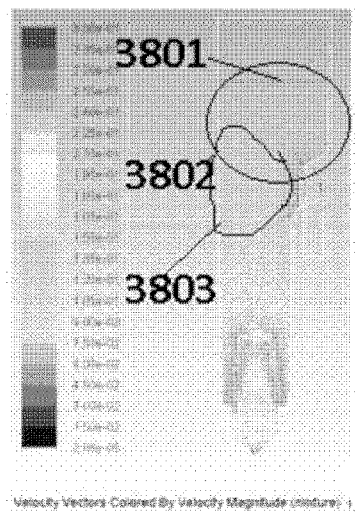
FIGS. 38*a-b* show z-section views the velocity distribution vectors with a 75% filling level and an inlet velocity of 0.52 m/s.
Figure 38B:
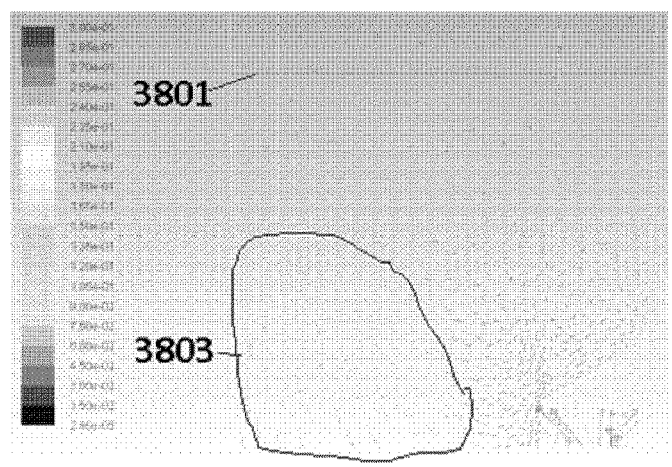

FIGS. 38a and 38b show section views of the velocity distribution vectors in the plane at z=0, or the symmetry plane. FIG. 38b is a close up view of the area in circle 3802 of FIG. 38a. In each of FIGS. 38a and 38b, line 3801 represents the filling level, set at 75%. The legend for FIGS. 38a-b transitions from a high velocity flow in red at 3.00 e-01 m/s, orange at 2.38e-01 m/s, yellow at 2.03e-01 m/s, green at 1.42e-01 m/s to light blue at 6.75e-02 m/s to a low velocity flow shown in blue at 2.86e-05 m/s. Area 3803 is green, while the remainder of the diagrams are in blue.

As shown in FIGS. 38a and 38b, there are no observable areas of stagnant flow. Additionally, areas of circular flow have been eliminated. Velocity in the small diameter cylinder portion of the venous air capture chamber is uniform under the conditions.

Figure 39A:
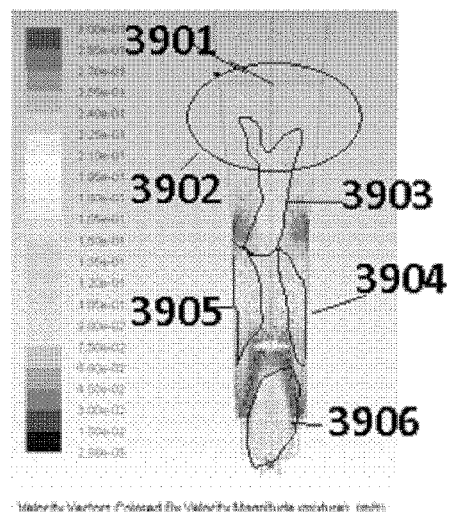
FIGS. 39*a-b* show x-section views the velocity distribution vectors with a 75% filling level and an inlet velocity of 0.52 m/s.
Figure 39B:
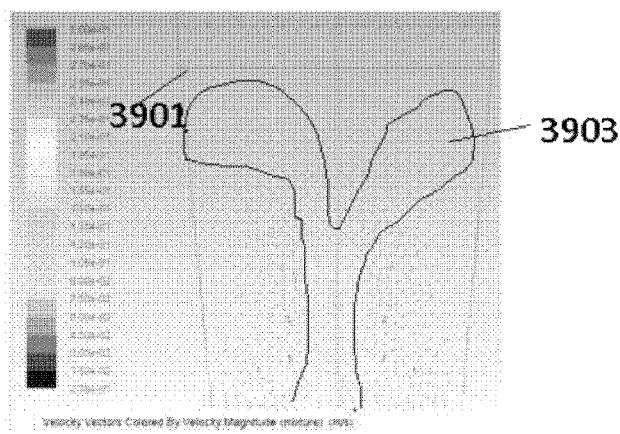

FIGS. 39a and 39b show section views of the velocity distribution chambers at a section of x=0, which is across a center line of the small diameter cylinder portion. In each of FIGS. 39a and 39b, the line marked 3901 represents the filling level of 75%. FIG. 39b is a close up view of the area in FIG. 39a shown in circle 3902. The legend for FIGS. 39a-b transitions from a high velocity flow in red at 3.00 e-01 m/s, orange at 2.48e-01 m/s, yellow at 2.03e-01 m/s, green at 1.42e-01 m/s to light blue at 6.75e-02 m/s to a low velocity flow shown in blue at 2.86e-05 m/s. Areas 3903 and 3906 are green, areas 3904 and 3905 are light blue, and the remainder of the diagram is in blue. As shown, there are no areas of stagnant flow within the venous air capture chamber. Further, areas of circular flow are eliminated in the views shown in FIGS. 39a and 39b.

Figure 40A:
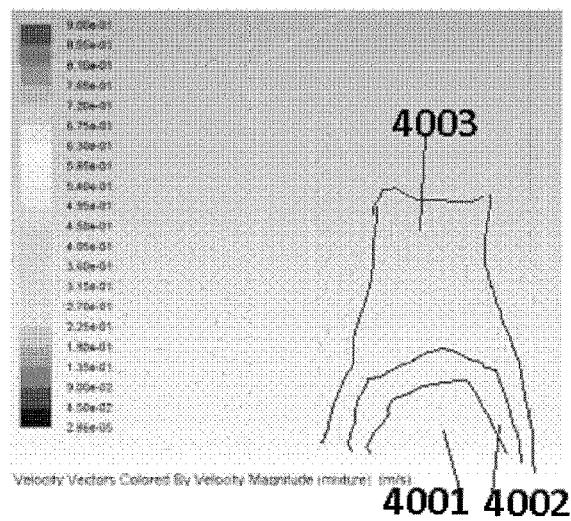
FIGS. 40*a-b* show velocity distribution vectors near the inlet ports with a 75% filling level and an inlet velocity of 0.52 m/s.
Figure 40B:
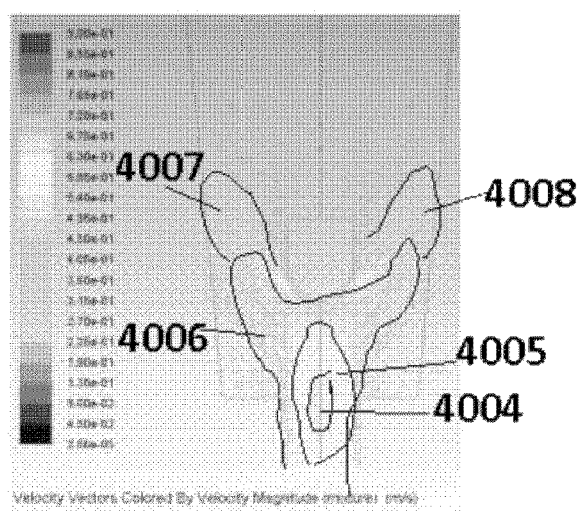

FIGS. 40a and 40b illustrate velocity distribution within the inlet ports. The legend for FIGS. 40a-b transitions from a high velocity flow in red at 9.00 e-01 m/s, orange at 7.43e-01 m/s, yellow at 6.07e-01 m/s, green at 4.29e-01 m/s to light blue at 2.48e-01 m/s to a low velocity flow shown in blue at 2.86e-05 m/s. FIG. 40a includes red portion 4001, yellow portion 4002, and green portion 4003. FIG. 40b includes red portion 4004, yellow portion 4005, green portion 4006, and light blue portions 4007 and 4008. As shown in FIGS. 40a and 40b, there are no low velocity or stagnant flow areas within the inlet ports.

Figure 41:
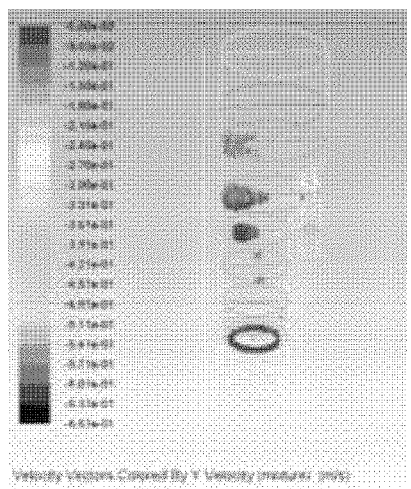
FIG. 41 shows velocity distribution vectors in the y-direction with a 75% filling level and an inlet velocity of 0.52 m/s.

FIG. 41 shows section views of the velocity in the y-direction through the chamber body through multiple sectional planes. In FIG. 41, the max velocity scale is set at 0.06 m/s, meaning only velocities in excess of 0.06 m/s are shown. As shown in FIG. 41, velocities in excess of 0.06 m/s can be found at the Y=6 cm, Y=5 cm, and Y=4 cm planes, but not at the Y=3 cm plane. The legend for FIG. 41 transitions from a low velocity flow in red at −6.00 e-02 m/s, orange at −1.95e-01 m/s, yellow at −2.55e-01 m/s, green at −3.76e-01 m/s to light blue at −4.96e-01 m/s to a high velocity flow shown in blue at −6.61e-01 m/s. All visible velocity vectors are shown in red meaning that Y-direction velocities in some portions of the small diameter cylinder portion of the venous air capture chamber are maintained at less than 0.06 m/s.

Figure 42:
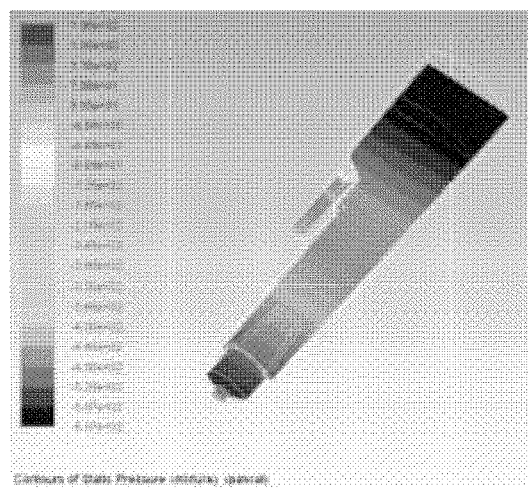
FIG. 42 shows the pressure distribution in the venous air capture chamber with a 75% filling level and an inlet velocity of 0.52 m/s.

FIG. 42 is a representative pressure distribution within the venous air capture chamber, which shows the pressure distribution. At the conditions of a 500 ml/min flow rate, the pressure ranges from −607 to 116 Pa or −4.5 mmHg to 0.87 mmHg. The legend in FIG. 42 transitions from red at 1.96e+02 pascal, to orange at −5.56e+01 pascal, yellow at −6.49e+01 pascal, green at −2.25e+02 pascal, to light blue at −3.86e+02 pascal, to a low in blue of −6.07e+02 pascal. The pressure is greatest near the outlet of the venous air capture chamber, and decreases with increasing height through the venous air capture chamber. The pressure is greatest near the outlet of the venous air capture chamber, and decreases with increasing height through the venous air capture chamber.

Figure 43A:
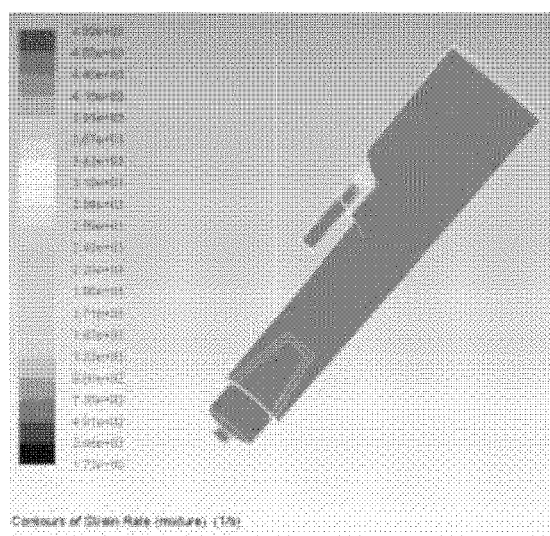
FIGS. 43*a-c* show the max shear rate with a 75% filling level and an inlet velocity of 0.52 m/s.
Figure 43B:
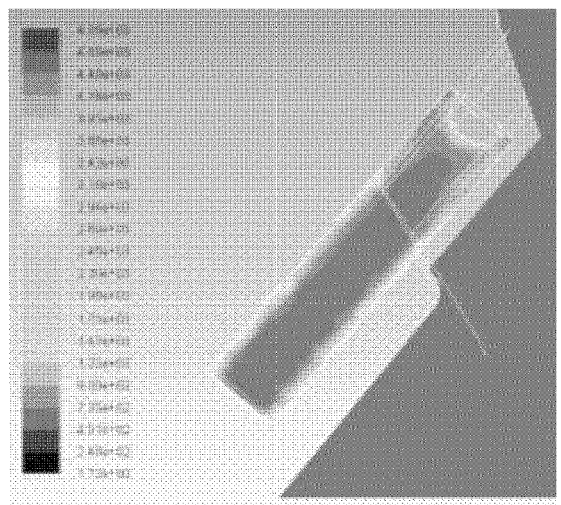
Figure 43C:
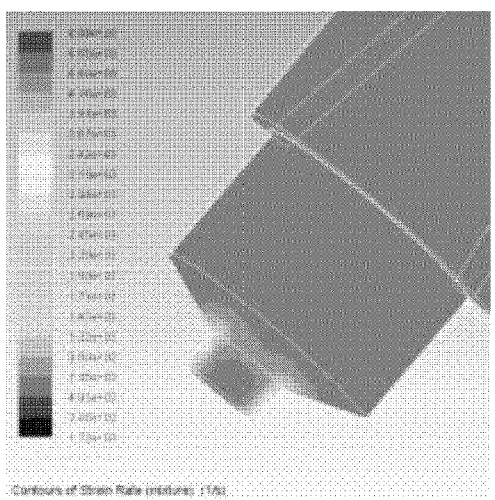

FIG. 43a shows a representative strain distribution within the chamber body at a plane of z=0, which is a proper representation to show strain distribution. FIGS. 43b and 44c are the representative strain distributions near the fluid inlet and fluid outlet, respectively. The legend for FIG. 43a-c transitions from a shear stress in red at 4.89 e+03 l/s, orange at 3.79e+03 l/s, yellow at 3.30e+03 l/s, green at 2.37e+03 l/s to light blue at 1.10e+03 l/s to a low shear stress shown in blue at 1.72 l/s. All visible shear stress is shown in green. As shown in FIG. 43a, the maximum shear rate is about 4890 l/s or a max shear stress (considering a viscosity of 0.00271 PaS) of 13.3 Pa, which is much less than the safety thresholds. As such, the venous air capture chambers described can be safely used for a patient with an inlet flow velocity of 500 ml/min and a filling level of 75%. As shown in FIG. 43a, the highest levels of strain are concentrated at the fluid inlet and outlet. However, as shown in FIGS. 43b and 43c, the strain levels still remain well below the dangerous levels.

Figure 44:
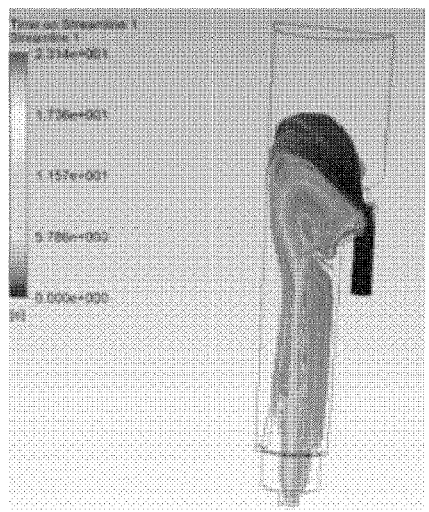
FIG. 44 shows residence time distributions with a 75% filling level and an inlet velocity of 0.52 m/s.

FIG. 44 shows a residence time distribution within the venous air capture chamber with the conditions of 500 ml/min inlet flow rate and a 75% filling level. As shown in FIG. 44, the maximum residence time is about 23 seconds. Due to limits of ANSYS Fluent, only a 3D residence time distribution is presented.

Experiment 9

Figure 45:
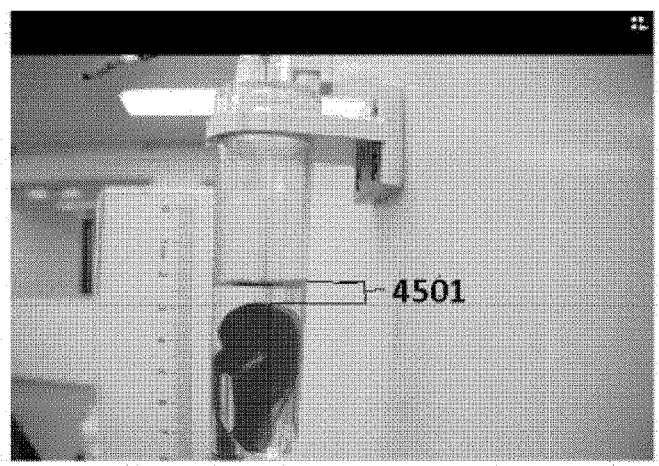
FIG. 45 shows a setup of an experiment to detect the presence of stagnant flow.

In vitro testing of the venous air capture chambers described was also carried out. In order to determine whether stagnant flow exists at particular combinations of filling levels and flow rates, dye was introduced at set flow rates into the venous air capture chambers, as shown in FIG. 45. The clear fluid in the area between the dye and the fluid-air interface, labeled as 4501 in FIG. 45 shows that a stagnant flow area exists.

Figure 46A:
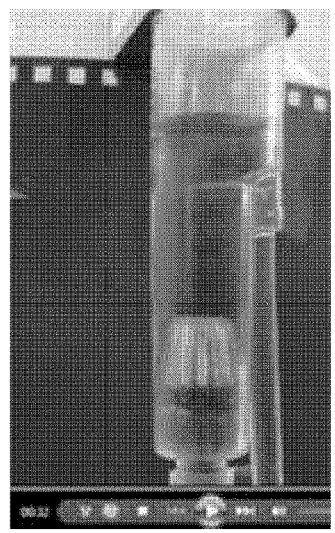
FIGS. 46*a-c* show the presence or absence of stagnant flow as a function of filling level for a flow rate of 50 mL/min.
Figure 46B:
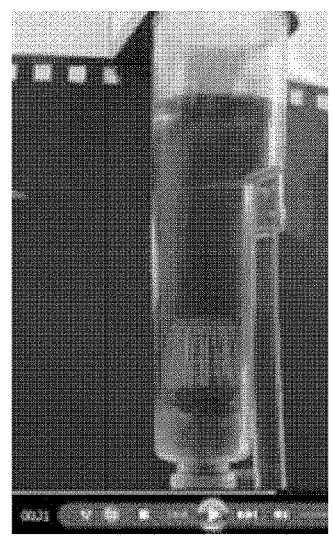
Figure 46C:
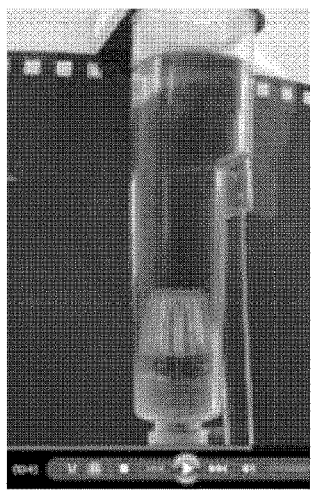

FIG. 46a shows the results of the testing carried out with a filling level of 50% and a flow rate of 50 mL/min. FIG. 46b shows the results of the testing carried out with a filling level of 55% and a flow rate of 50 mL/min. FIG. 46c shows the results of the testing carried out with a filling level of 65% and a flow rate of 50 mL/min. As shown in FIGS. 46a-c, at a flow rate of 50 mL/min, stagnant flow areas exist at any of the testing filling levels. Although the stagnant flow area shown in FIG. 46a is small, the stagnant flow area was confirmed through additional testing.

Figure 47A:
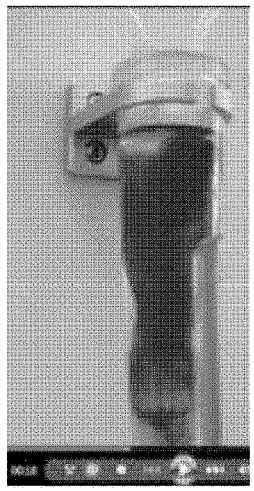
FIGS. 47*a-b* show the presence or absence of stagnant flow as a function of filling level for a flow rate of 100 mL/min.
Figure 47B:
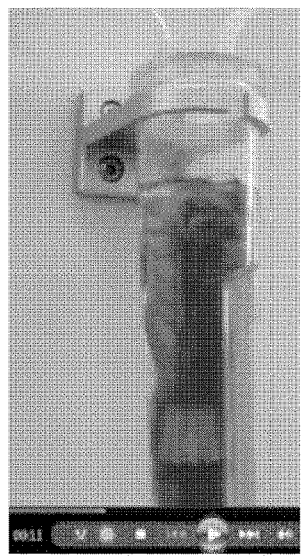

FIG. 47a shows results of the stagnant flow testing carried out for a flow rate of 100 mL/min and a filling level of 75%. FIG. 47b shows results of the stagnant flow testing carried out for a flow rate of 100 ml/min and a filling level of 65%. As shown in FIGS. 47a and 47b, a stagnant flow area exists for a flow rate of 100 mL/min and a 75% filling level but does not exist for a flow rate of 100 mL/min and a filling level of 65%.

Figure 48A:
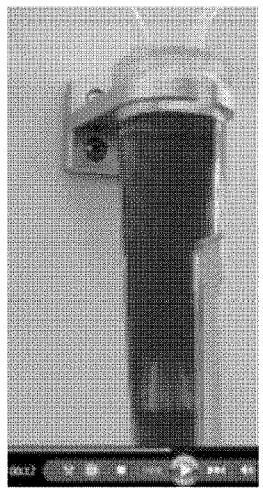
FIGS. 48*a-b* show the presence or absence of stagnant flow as a function of filling level for a flow rate of 275 mL/min.
Figure 48B:
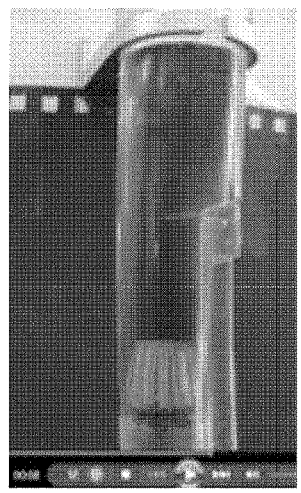

FIG. 48a shows results of the stagnant flow testing carried out for a flow rate of 275 mL/min and a filling level of 75%. FIG. 48b shows results of the stagnant flow testing carried out for a flow rate of 275 ml/min and a filling level of 85%. As shown in FIGS. 48a and 48b, no stagnant flow area exists for a flow rate of 275 mL/min and an either 75% filling level or a 85% filling level.

Figure 49A:
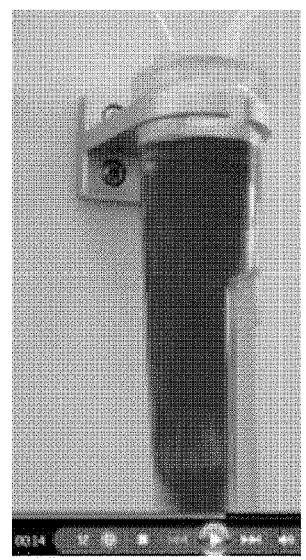
FIGS. 49*a-b* how the presence or absence of stagnant flow as a function of filling level for a flow rate of 500 mL/min.
Figure 49B:
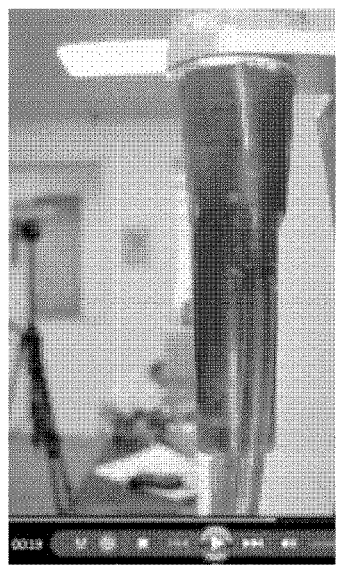

FIG. 49a shows results of the stagnant flow testing carried out for a flow rate of 500 mL/min and a 75% filling level. FIG. 49b shows results of the stagnant flow testing carried out for a flow rate of 500 mL/min and a 85% filling level. As shown in FIGS. 49a and 49b, no stagnant flow area exists for a flow rate of 500 mL/min and either a 75% filling level or an 85% filling level.

The results of the stagnant flow testing are presented in Table 1. Experiments resulting in stagnant flow areas are labeled Y in Table 1, and experiments without stagnant flow areas are labeled N. N/A shows combinations that were not tested.

TABLE 1

Existence of Stagnant Flow for Filling levels and Flow Rates
High Limit of Filling Level For Venous Chamber

| Flow rate | Filling Level | | | | |
|---|---|---|---|---|---|
| (ml/min) | 50% | 55% | 65% | 75% | 85% |
| 50 | Y | Y | Y | N/A | N/A |
| 100 | N/A | N/A | N | Y | N/A |
| 275 | N/A | N/A | N/A | N | N |
| 500 | N/A | N/A | N/A | N | N |

As shown in Table 1, there are no stagnant flows observed for 65% filling level at 100 ml/min, and 75% filling levels at 275 ml/min and 500 ml/min. The 85% filling level was tested also at 275 and 500 ml/min flow rates with no stagnant flows.

Experiment 10

Figure 50:
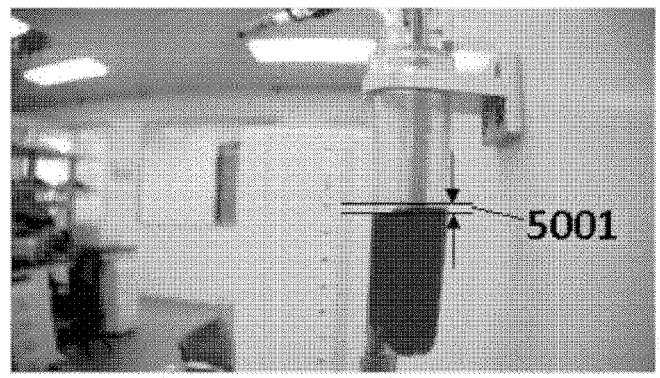
FIG. 50 shows a setup of an experiment to determine whether an unstable area exists in the fluid-air interface.

In order to test the lower limit of the fill level, the experiments were conducted to determine whether a stable fluid-air interface could exist for a given combination of flow rate and filling level by determining the height of unstable fluid at the fluid-air interface. As shown in FIG. 50, at the height of the unstable area of the fluid-air interface was measured, shown as height 5001. If the height 5001 is greater than 3 mm, an unstable fluid-air interface was confirmed.

Figure 51:
FIG. 51 shows a stable interface existing with a flow rate of 50 mL/min and a filling level of 50%.

FIG. 51 illustrates the result of the fluid-air interface testing at a flow rate of 50 mL/min and a filling level of 50%. As shown in FIG. 51, a stable interface exists at a flow rate of 50 mL/min and a filling level of 50%.

Figure 52:
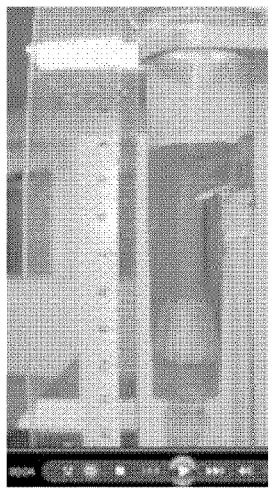
FIG. 52 shows a stable interface existing with a flow rate of 100 mL/min and a filling level of 50%.

FIG. 52 illustrates the result of the fluid-air interface testing at a flow rate of 100 mL/min and a filling level of 50%. As shown in FIG. 52, a stable interface exists at a flow rate of 100 mL/min and a filling level of 50%.

Figure 53A:
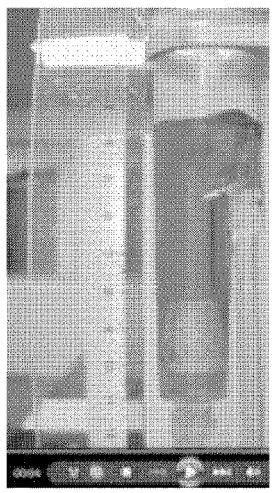
FIGS. 53*a-b* the presence or absence of a stable fluid-air interface with a flow rate of 275 mL/min as a function of filling level.
Figure 53B:
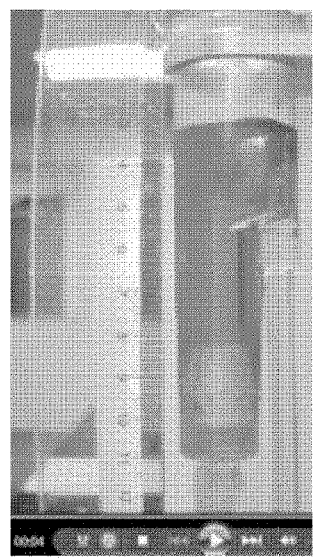

FIG. 53*a* illustrates the results of the fluid air-interface testing at a flow rate of 275 mL/min and a filling level of 60%. FIG. 53*b* illustrates the results of the fluid air-interface testing at a flow rate of 275 mL/min and a filling level of 65%. As shown in FIGS. 53*a* and 53*b*, a stable interface exists for a flow rate of 275 mL/min at a filling level of 65%, but an unstable interface exists at a filling level of 60%.

Figure 54A:
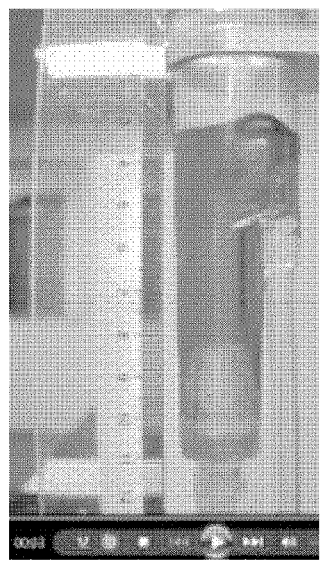
FIGS. 54*a-b* the presence or absence of a stable fluid-air interface with a flow rate of 500 mL/min as a function of filling level.
Figure 54B:
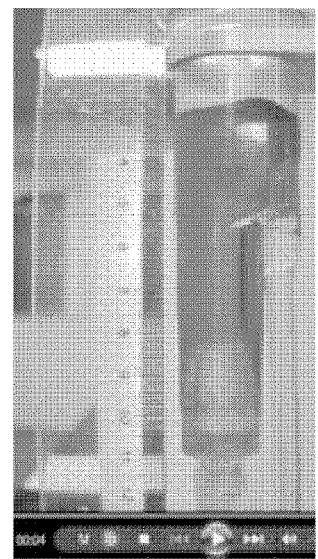

FIG. 54*a* illustrates the results of the fluid air-interface testing at a flow rate of 500 mL/min and a filling level of 65%. FIG. 54*b* illustrates the results of the fluid air-interface testing at a flow rate of 500 mL/min and a filling level of 70%. As shown in FIGS. 54*a* and 54*b*, a stable interface exists for a flow rate of 500 mL/min at a filling level of 70%, but an unstable interface exists at a filling level of 65%.

The results of the fluid-air interface testing are summarized in Table 2. In Table 2, a Y denotes an unstable interface, while an N denotes a stable interface. As shown, a stable interface is maintained at a flow rate of 50 mL/min with a 50% filling level; at 100 mL/min with a 50% filling level; at 275 mL/min with a 65% filling level, and at 500 mL/min with a 70% filling level.

TABLE 2

Existence of Stable Interface for Filling Volumes and Flow Rates
Low Limit of Filling Level For Venous Chamber

| Flow rate | Filling Level | | | |
|---|---|---|---|---|
| (ml/min) | 50% | 60% | 65% | 70% |
| 50 | N | N/A | N/A | N/A |
| 100 | N | N/A | N/A | N/A |
| 275 | N/A | Y | N | N/A |
| 500 | N/A | N/A | Y | N |

Based on the data presented in Experiments 9 and 10, a specified filling level of 50% to 65% is suggested for a flow rate of 100 mL/min; a specified filling level of 65% to 85% is suggested for a flow rate of 275 mL/min; and a specified filling level of between 70% and 85% is suggested for a flow rate of 500 mL/min. Therefore, a specified filling level of 50% to 65% could be used with a flow rate of 100 mL/min, while a specified filling level of between 70% and 85% could be used with flow rates of 275 mL/min or greater. In any embodiment, the specified filling level can be 40% to 65% when the blood flow rate is between 50 mL/min and 200 mL/min; the specified filling level can be between 50% to 75% when the blood flow rate is between 100 mL/min and 275 mL/min; the specified filling level can be between 65% to 85% when the blood flow rate is between 275 mL/min and 500 mL/min; and the specified filling level can be between 70% to 85% when the blood flow rate is 500 mL/min or greater.

Experiment 11

The residence time of fluid in the venous air capture chambers was also determined by determining the amount of time for all of the dye to pass through the outlet. Results are summarized in Table 3. As shown in Table 3, the residence time varied from between 11 seconds for a 65% filling level at 500 mL/min to about 76 seconds for a 50% filling level at 50 mL/min.

TABLE 3

Residence time for Flow Rates and Filling Volumes
Residence Time

| Flow rate | Filling Level | | | |
|---|---|---|---|---|
| (ml/min) | 50% | 60% | 65% | 70% |
| 50 | 76 | N/A | N/A | N/A |
| 100 | N/A | 58 | 54 | N/A |
| 275 | N/A | 23 | 27 | 36 |
| 500 | N/A | 16 | 11 | 17 |

Experiment 12

In order to ensure air bubbles can be captured by the venous air capture chambers, bubble visualization testing was carried out. Bubble flow was visualized at filling level of 75% and a flow rate starting from 500 ml/min, and then 400 ml/min if bubbles were observed to pass through the fluid outlet, and then 300 ml/min. A ruler was used for measuring bubble size. A picture was taken from video, including the ruler, and then was loaded into the Solidworks. Under 2D, the bubble size was calculated, by compared the bubble's dimension and ruler's scale of 1 mm. Very few bubbles were passed through the fluid outlet at a flow rate of 500 ml/min, with no bubble passing at 400 ml/min. The bubble size at 500 ml/min was about 0.89 to 1.06 mm diameter, and about 0.91 to 1.07 mm diameter at 400 ml/min.

One skilled in the art will understand that various combinations and/or modifications and variations can be made in the described systems and methods depending upon the specific needs for operation. Moreover features illustrated or described as being part of an aspect of the invention may be used in the aspect of the invention, either alone or in combination.

We claim:

1. A venous air capture chamber, comprising:
   a chamber body comprising a top portion and a bottom portion;
   a fluid inlet upwardly extending from the bottom portion of the chamber body towards the top portion of the chamber body to form a fluid inlet tube terminating in a first fluid inlet port and a second fluid inlet port; wherein the first fluid inlet port and the second fluid inlet port are tangential to a circle plane formed by a center axis of the chamber body; wherein the first fluid inlet port and second fluid inlet port are opposedly positioned on the fluid inlet at an angle of 180° or close to 180°; and
   a fluid outlet on the bottom portion of the chamber body;
   wherein the chamber body comprises a small cylinder portion and a large cylinder portion;
   wherein the large cylinder portion is positioned higher relative to the small cylinder portion of the chamber; and wherein the first fluid inlet port and second fluid inlet port are positioned flush with a base of the large cylinder portion.

2. The venous air capture chamber of claim 1, wherein the first fluid inlet port and second fluid inlet port are positioned at a 90° turn or close to a 90° turn relative to a fluid flow of the tube.

3. The venous air capture chamber of claim 1, wherein the fluid outlet comprises a mesh filter forming a cylindrical taper having a decreasing diameter in an upward direction from the bottom of the chamber and terminates in a substantially planar surface.

4. The venous air capture chamber of claim 1, wherein the chamber body is a substantially ovoid.

5. The venous air capture chamber of claim 1, wherein the fluid inlet is positioned in the chamber body in the large cylinder portion; and wherein the fluid outlet is positioned on a bottom of the small cylinder portion.

6. The venous air capture chamber of claim 1, wherein the chamber body has a height of between 9 and 13 cm.

7. The venous air capture chamber of claim 6, wherein the small cylinder portion has a height of between 3 and 7 cm.

8. The venous air capture chamber of claim 6, wherein the large cylinder portion has a height of between 4 and 8 cm.

9. The venous air capture chamber of claim 1, wherein the small cylinder portion is inwardly sloping from a top of the small cylinder portion to the bottom of the small cylinder portion.

10. The venous air capture chamber of claim 1, further comprising a spiral flow inducing shelf positioned inside the chamber body at the fluid inlet flush to a bottom portion of the fluid inlet.

11. The venous air capture chamber of claim 10, wherein the spiral flow inducing shelf is downwardly sloping.

12. The venous air capture chamber of claim 1, further comprising a cap covering the top portion of the chamber body.

13. The venous air capture chamber of claim 12, wherein the cap comprises two ports.

14. A extracorporeal flow path, comprising:
    a dialyzer comprising a blood side of the dialyzer and a dialysate side of the dialyzer;
    a blood inlet fluidly connected to the blood side of the dialyzer and a blood outlet fluidly connected to the blood side of the dialyzer;
    a blood pump; and
    the venous drip chamber of claim 1 positioned in a venous blood line fluidly connectable to a patient and to the dialyzer.

15. The extracorporeal flow path of claim 14, further comprising an arterial air capture chamber positioned in an arterial blood line fluidly connectable to the dialyzer and to a patient.

16. A method of performing dialysis, comprising the steps of:
    pumping blood through the extracorporeal flow path of claim 15; and
    pumping dialysate through the dialysate side of the dialyzer; wherein the step of pumping blood through the extracorporeal flow path comprises controlling the blood pump to pump the blood at a blood flow rate of between 50 mL/min and 500 mL/min.

17. The method of claim 16, further comprising the step of filling the venous air capture chamber to a specified filling level; wherein the specified filling level is based on the blood flow rate.

18. The method of claim 17, wherein the specified filling level is between 40% to 65% when the blood flow rate is between 50 mL/min and 200 mL/min; the specified filling level is between 50% to 75% when the blood flow rate is between 100 mL/min and 275 mL/min; the specified filling level is between 65% to 85% when the blood flow rate is between 275 mL/min and 500 mL/min; and the specified filling level is between 70% to 85% when the blood flow rate is 500 mL/min or greater.

19. The method of claim 17, wherein the blood flow rate is between 275 and 500 mL/min and the specified filling level is between 65% and 80%.

20. A method for priming a dialyzer, comprising the steps of:
    pumping physiologically compatible saline through the extracorporeal flow path of claim 14; and
    pumping physiologically compatible saline through the dialysate side of the dialyzer.

* * * * *